(12) United States Patent
Mier et al.

(10) Patent No.: US 10,513,539 B2
(45) Date of Patent: *Dec. 24, 2019

(54) HYDROPHOBIC MODIFIED PEPTIDES AND THEIR USE FOR LIVER SPECIFIC TARGETING

(75) Inventors: Walter Mier, Bensheim (DE); Stephan Urban, Neustadt-Weinstrasse (DE); Stefan Mehrle, Limburgerhof (DE); Uwe Haberkorn, Schwetzingen (DE)

(73) Assignee: Ruprecht-Karls-Universitat Heidelberg, Heidelberg (DE)

( * ) Notice: Subject to any disclaimer, the term of this patent is extended or adjusted under 35 U.S.C. 154(b) by 33 days.

This patent is subject to a terminal disclaimer.

(21) Appl. No.: 13/984,694

(22) PCT Filed: Feb. 10, 2012

(86) PCT No.: PCT/EP2012/052349
§ 371 (c)(1),
(2), (4) Date: Oct. 18, 2013

(87) PCT Pub. No.: WO2012/107579
PCT Pub. Date: Aug. 16, 2012

(65) Prior Publication Data
US 2014/0038886 A1    Feb. 6, 2014

Related U.S. Application Data

(60) Provisional application No. 61/441,492, filed on Feb. 10, 2011.

(51) Int. Cl.
| *C07K 7/08* | (2006.01) |
| *A61K 51/04* | (2006.01) |
| *A61K 51/08* | (2006.01) |
| *C07K 14/00* | (2006.01) |
| *A61K 47/54* | (2017.01) |
| *A61K 47/64* | (2017.01) |

(52) U.S. Cl.
CPC ............... *C07K 7/08* (2013.01); *C07K 14/00* (2013.01)

(58) Field of Classification Search
None
See application file for complete search history.

(56) References Cited

FOREIGN PATENT DOCUMENTS

| JP | 2001-523961 | 11/2001 | |
| JP | 2007-525997 | 9/2007 | |
| JP | 2014-506574 | 3/2014 | |
| JP | 2014-510050 | 4/2014 | |
| JP | 2017-081952 | 5/2017 | |
| WO | WO 2009/092396 A1 | 7/2009 | |
| WO | WO 2009/092612 A1 | 7/2009 | |
| WO | WO 2009092611 A1 * | 7/2009 | ............ A61K 39/292 |
| WO | WO-2009092612 A1 * | 7/2009 | ............ A61K 38/162 |
| WO | 2009/100934 | 8/2009 | |
| WO | 2010/088411 | 8/2010 | |

OTHER PUBLICATIONS

Al Ghamdi et al. Synergistic interaction between lipid-loading and doxorubicin exposure in Huh7 hepatoma cells results in enhanced cytotoxicity and cellular oxidative stress: implications for acute and chronic care of obese cancer patients. Toxicology Research 4.6 (2015): 1479-1487.*
Bowie et al. Deciphering the message in protein sequences: tolerance to amin oacid substitutions. Science, 1990, 247:1306-1310.*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. Journal of Cell Biology, 111:2129-2138, 1990.*
Lazar et al. Transforming growth factor alpha: mutation of aspartic acid 47 and leucine 48 results in different biological activities. Molecular Cellular Biology, 8:1247-1252, 1988.*
Bork. Powers and pitfalls in sequence analysis: the 70% hurdle. Genome Research, 2000,10:398-400.*
Gripon et al. Efficient Inhibition of Hepatitis B Virus Infection by Acylated Peptides Derived from the Large Viral Surface Protein. Journal of Virology, 2005; 79(3):1613-1622.*
Toita et al. Applications of human hepatitis B virus preS domain in bio- and nanotechnology. World Journal of Gastroenterology, 2015; 21(24):7400-7411.*
Greenfield et al. Recent advacnes in nonalcoholic fatty liver disease. Current Opinion in Gastroenterology, 2008; 24:320-327.*
Zhu. Systemic Therapy of Advanced Hepatocellular Carcinoma: How Hopeful Should We Be?The Oncologist, 2006; 11:790-800.*
Greenfield et al. Current Opinion in Gastroenterology, 2008; 24:320-327 (Year: 2008).*
Al Ghamdi et al. Toxicology Research 4.6 (2015): 1479-1487 (Year: 2015).*
Bowie et al. Science, 1990, 247:1306-1310 (Year: 1990).*
Burgess et al. J. Cell Biol. 111:2129-2138, 1990 (Year: 1990).*
Lazar et al. Mol. Cell. Biol., 8:1247-1252, 1988 (Year: 1988).*
Bork. Genome Research, 2000,10:398-400 (Year: 2000).*
Gripon et al. Journal of Virology, 2005; 79(3):1613-1622 (Year: 2005).*
Toita et al. (World Journal of Gastroenterology, 2015; 21(24):7400-7411 (Year: 2015).*

(Continued)

*Primary Examiner* — Vanessa L. Ford
*Assistant Examiner* — Sandra E Dillahunt
(74) *Attorney, Agent, or Firm* — Barnes & Thornburg LLP

(57) ABSTRACT

The present invention relates to hydrophobic modified peptides for the specific delivery of compounds to the liver, preferably to hepatocytes, in vitro as well as in vivo. The present invention relates to pharmaceutical compositions comprising said hydrophobic modified peptide(s) and the compound(s) to be specifically delivered to the liver. The present invention furthermore relates to the use of the inventive hydrophobic modified peptides as well as to a method for the prevention and/or treatment of liver diseases or disorders.

38 Claims, 7 Drawing Sheets
Specification includes a Sequence Listing.

(56) References Cited

OTHER PUBLICATIONS

Zhu. The Oncologist, 2006; 11:790-800 (Year: 2006).*
Majunndar et al. Ailment Pharmacol Ther 2016; 43:1276-1292 (Year: 2016).*
Official action from related JP 2014-506574 dated Dec. 8, 2015, 6 pages.
"Development of a novel fluorogenic proteolytic beacon for in vivo detection and imaging of tumour-associated matrix metalloproteinase-7 activity", Biochemical Journal, 2004, vol. 377, pp. 617-628.
Luis M De Leon-Rodriguez and Zoltan Kovacs: "The Synthesis and Chelation Chemistry of DOTA", BIoconjugate Chemistry, ACS, Washington, DC, US, vol. 19, No. 2, Feb. 1, 2008 (Feb. 1, 2008), pp. 391-402, XP008146824, ISSN: 1043-1802, DOI: 10.1021/BC700328S, Retrieved from teh Internet: URL:http//pubs.acs.org/doi/abs/10.1021/bc700328s [retrieved on Dec. 12, 2007] p. 392, right-hand-column, para 4-5, p. 366, right-hand, para 4, p. 398.
Slimit Majlimdar and Teruna J. Siabaan: Medicinal Research Reviews: Peptide-Mediated Targeted Drug Delivery, vol. 32, Issue 3, pp. 637-658, May 2012.
Sumit Majumdar and Teruna J. Siabaan, Peptide-Mediated Targeted Drug Delivery, Medical Research Reviews, 32 No. 3, 637-658, 2012, published online Sep. 2, 2010 in Wiley InterScience (www.interscience.wiley.com), DOI 10.1002/med.20225.
Luis M. De Leon-Rodriguez and Zoltan Kovacs, The Synthesis and Chelation Chemistry of DOTA—Peptide Conjugates, Copyright by the American Chemical Society, Feb. 2008, vol. 19, No. 2.
Search Report for Chinese Application No. 2012800082246.

* cited by examiner

HM = Hydrophobic Modification $T_x$ = Therapeutic

SEQUENCE LISTING

```
<160> NUMBER OF SEQ ID NOS: 21

<210> SEQ ID NO 1
<211> LENGTH: 7
<212> TYPE: PRT
<213> ORGANISM: Hepatitis B virus
<220> FEATURE:
<221> NAME/KEY: VARIANT
<222> LOCATION: (6)..(6)
<223> OTHER INFORMATION: Arbitrary amino acid, preferably F or L, more
      preferably F

<400> SEQUENCE: 1

Asn Pro Leu Gly Phe Xaa Pro
1               5

<210> SEQ ID NO 2
<211> LENGTH: 119
<212> TYPE: PRT
<213> ORGANISM: Hepatitis B virus

<400> SEQUENCE: 2

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
        35                  40                  45

Lys Asp His Trp Pro Gln Ala Asn Gln Val Gly Val Gly Ala Phe Gly
    50                  55                  60
```

Pro Gly Phe Thr Pro Pro His Gly Gly Val Leu Gly Trp Ser Pro Gln
65                  70                  75                  80

Ala Gln Gly Ile Leu Ala Thr Val Pro Ala Met Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala
            115

<210> SEQ ID NO 3
<211> LENGTH: 119
<212> TYPE: PRT
<213> ORGANISM: Hepatitis B virus

<400> SEQUENCE: 3

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Lys Ala Asn Ser Glu Asn Pro Asp Trp Asp Leu Asn Pro His
            35                  40                  45

Lys Asp Asn Trp Pro Asp Ala His Lys Val Gly Val Gly Ala Phe Gly
        50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala
            115

<210> SEQ ID NO 4
<211> LENGTH: 119
<212> TYPE: PRT
<213> ORGANISM: Hepatitis B virus

<400> SEQUENCE: 4

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
                20                  25                  30

Ala Phe Lys Ala Asn Ser Glu Asn Pro Asp Trp Asp Leu Asn Pro His
            35                  40                  45

Lys Asp Asn Trp Pro Asp Ala His Lys Val Gly Val Gly Ala Phe Gly
        50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala
            115

<210> SEQ ID NO 5

<211> LENGTH: 108
<212> TYPE: PRT
<213> ORGANISM: Hepatitis B virus

<400> SEQUENCE: 5

```
Met Gly Gln Asn Leu Ser Thr Ser Asn Pro Leu Gly Phe Phe Pro Glu
1               5                   10                  15
His Gln Leu Asp Pro Ala Phe Lys Ala Asn Thr Asn Asn Pro Asp Trp
            20                  25                  30
Asp Phe Asn Pro Lys Lys Asp Tyr Trp Pro Glu Ala Asn Lys Val Gly
        35                  40                  45
Ala Gly Ala Phe Gly Pro Gly Phe Thr Pro Pro His Gly Gly Leu Leu
    50                  55                  60
Gly Trp Ser Pro Gln Ala Gln Gly Ile Leu Thr Thr Leu Pro Ala Asn
65                  70                  75                  80
Pro Pro Pro Ala Ser Thr Asn Arg Gln Ser Gly Arg Gln Pro Thr Pro
                85                  90                  95
Leu Ser Pro Pro Leu Arg Asp Thr His Pro Gln Ala
            100                 105
```

<210> SEQ ID NO 6
<211> LENGTH: 108
<212> TYPE: PRT
<213> ORGANISM: Hepatitis B virus

<400> SEQUENCE: 6

```
Met Gly Gln Asn Leu Ser Thr Ser Asn Pro Leu Gly Phe Phe Pro Asp
1               5                   10                  15
His Gln Leu Asp Pro Ala Phe Arg Ala Asn Thr Asn Asn Pro Asp Trp
            20                  25                  30
Asp Phe Asn Pro Asn Lys Asp Thr Trp Pro Asp Ala Asn Lys Val Gly
        35                  40                  45
Ala Gly Ala Phe Gly Leu Gly Phe Thr Pro Pro His Gly Gly Leu Leu
    50                  55                  60
Gly Trp Ser Pro Gln Ala Gln Gly Ile Met Gln Thr Leu Pro Ala Asn
65                  70                  75                  80
Pro Pro Pro Ala Ser Thr Asn Arg Gln Ser Gly Arg Gln Pro Thr Pro
                85                  90                  95
Leu Ser Pro Pro Leu Arg Thr Thr His Pro Gln Ala
            100                 105
```

<210> SEQ ID NO 7
<211> LENGTH: 118
<212> TYPE: PRT
<213> ORGANISM: Hepatitis B virus

<400> SEQUENCE: 7

```
Met Gly Leu Ser Trp Thr Val Pro Leu Glu Trp Gly Lys Asn Ile Ser
1               5                   10                  15
Thr Thr Asn Pro Leu Gly Phe Phe Pro Asp His Gln Leu Asp Pro Ala
            20                  25                  30
Phe Arg Ala Asn Thr Arg Asn Pro Asp Trp Asp His Asn Pro Asn Lys
        35                  40                  45
Asp His Trp Thr Glu Ala Asn Lys Val Gly Val Gly Ala Phe Gly Pro
    50                  55                  60
Gly Phe Thr Pro Pro His Gly Gly Leu Leu Gly Trp Ser Pro Gln Ala
65                  70                  75                  80
```

Gln Gly Met Leu Lys Thr Leu Pro Ala Asp Pro Pro Ala Ser Thr
            85                  90                  95

Asn Arg Gln Ser Gly Arg Gln Pro Thr Pro Ile Thr Pro Leu Arg
            100                 105                 110

Asp Thr His Pro Gln Ala
            115

<210> SEQ ID NO 8
<211> LENGTH: 119
<212> TYPE: PRT
<213> ORGANISM: Hepatitis B virus

<400> SEQUENCE: 8

Met Gly Ala Pro Leu Ser Thr Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
            35                  40                  45

Lys Asp Ser Trp Pro Met Ala Asn Lys Val Gly Val Gly Gly Tyr Gly
        50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Ala Ser
            85                  90                  95

Thr Asn Arg Arg Ser Gly Arg Lys Pro Thr Pro Val Ser Pro Pro Leu
            100                 105                 110

Arg Asp Thr His Pro Gln Ala
            115

<210> SEQ ID NO 9
<211> LENGTH: 118
<212> TYPE: PRT
<213> ORGANISM: Hepatitis B virus

<400> SEQUENCE: 9

Met Gly Leu Ser Trp Thr Val Pro Leu Glu Trp Gly Lys Asn Leu Ser
1               5                   10                  15

Ala Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
            35                  40                  45

Asp Pro Trp Pro Glu Ala Asn Lys Val Gly Val Gly Ala Tyr Gly Pro
        50                  55                  60

Gly Phe Thr Pro Pro His Gly Gly Leu Leu Gly Trp Ser Pro Gln Ser
65                  70                  75                  80

Gln Gly Thr Leu Thr Thr Leu Pro Ala Asp Pro Pro Ala Ser Thr
            85                  90                  95

Asn Arg Gln Ser Gly Arg Gln Pro Thr Pro Ile Ser Pro Pro Leu Arg
            100                 105                 110

Asp Ser His Pro Gln Ala
            115

<210> SEQ ID NO 10
<211> LENGTH: 108
<212> TYPE: PRT
<213> ORGANISM: Hepatitis B virus

```
<400> SEQUENCE: 10

Met Gly Gln Asn His Ser Val Thr Asn Pro Leu Gly Phe Phe Pro Asp
1               5                   10                  15

His Gln Leu Asp Pro Leu Phe Arg Ala Asn Ser Asn Asn Pro Asp Trp
            20                  25                  30

Asp Phe Asn Pro Asn Lys Asp Thr Trp Pro Glu Ala Thr Lys Val Gly
        35                  40                  45

Val Gly Ala Phe Gly Pro Gly Phe Thr Pro Pro His Gly Gly Leu Leu
    50                  55                  60

Gly Trp Ser Pro Gln Ala Gln Gly Ile Leu Thr Thr Leu Pro Ala Ala
65                  70                  75                  80

Pro Pro Pro Ala Ser Thr Asn Arg Gln Ser Gly Arg Lys Ala Thr Pro
                85                  90                  95

Ile Ser Pro Pro Leu Arg Asp Thr His Pro Gln Ala
            100                 105

<210> SEQ ID NO 11
<211> LENGTH: 119
<212> TYPE: PRT
<213> ORGANISM: Hepatitis B virus

<400> SEQUENCE: 11

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Asn Trp Pro Met Ala Asn Lys Val Gly Val Gly Gly Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala
        115

<210> SEQ ID NO 12
<211> LENGTH: 108
<212> TYPE: PRT
<213> ORGANISM: Hepatitis B virus

<400> SEQUENCE: 12

Met Gly Gln Asn Leu Ser Val Ser Asn Pro Leu Gly Phe Phe Pro Glu
1               5                   10                  15

His Gln Leu Asp Pro Leu Phe Arg Ala Asn Thr Asn Asn Pro Asp Trp
            20                  25                  30

Asp Phe Asn Pro Asn Lys Asp Thr Trp Pro Glu Ala Thr Lys Val Gly
        35                  40                  45

Val Gly Ala Phe Gly Pro Gly Phe Thr Pro Pro His Gly Gly Leu Leu
    50                  55                  60

Gly Trp Ser Pro Gln Ala Gln Gly Val Thr Thr Ile Leu Pro Ala Val
65                  70                  75                  80

Pro Pro Pro Ala Ser Thr Asn Arg Gln Ser Gly Arg Gln Pro Thr Pro
```

```
                 85                  90                  95

Ile Ser Pro Pro Leu Arg Asp Thr His Pro Gln Ala
            100                 105

<210> SEQ ID NO 13
<211> LENGTH: 108
<212> TYPE: PRT
<213> ORGANISM: Hepatitis B virus

<400> SEQUENCE: 13

Met Gly Leu Asn Gln Ser Thr Phe Asn Pro Leu Gly Phe Phe Pro Ser
1               5                  10                  15

His Gln Leu Asp Pro Leu Phe Lys Ala Asn Ala Gly Ser Ala Asp Trp
            20                  25                  30

Asp Lys Asn Pro Asn Lys Asp Pro Trp Pro Gln Ala His Asp Thr Ala
        35                  40                  45

Val Gly Ala Phe Gly Pro Gly Leu Val Pro His Gly Gly Leu Leu
    50                  55                  60

Gly Trp Ser Ser Gln Ala Gln Gly Leu Ser Val Thr Val Pro Asp Thr
65                  70                  75                  80

Pro Pro Pro Pro Ser Thr Asn Arg Asp Lys Gly Arg Lys Pro Thr Pro
                85                  90                  95

Ala Thr Pro Pro Leu Arg Asp Thr His Pro Gln Ala
            100                 105

<210> SEQ ID NO 14
<211> LENGTH: 21
<212> TYPE: PRT
<213> ORGANISM: Hepatitis B virus

<400> SEQUENCE: 14

Lys Lys Lys Asn Leu Ser Thr Ser Asn Pro Leu Gly Phe Phe Pro Asp
1               5                  10                  15

His Gln Leu Pro Asp
            20

<210> SEQ ID NO 15
<211> LENGTH: 21
<212> TYPE: PRT
<213> ORGANISM: Hepatitis B virus

<400> SEQUENCE: 15

Lys Lys Lys Asn Leu Ser Thr Ser Asn Pro Leu Gly Phe Phe Pro Asp
1               5                  10                  15

His Gln Leu Asp Pro
            20

<210> SEQ ID NO 16
<211> LENGTH: 5
<212> TYPE: PRT
<213> ORGANISM: Hepatitis B virus
<220> FEATURE:
<221> NAME/KEY: VARIANT
<222> LOCATION: (2)..(2)
<223> OTHER INFORMATION: Arbitrary amino acid, preferably L, I or Q,
      more preferably L
<220> FEATURE:
<221> NAME/KEY: VARIANT
<222> LOCATION: (4)..(4)
<223> OTHER INFORMATION: Arbitrary amino acid, preferably T, V, A or is
      not present, more preferably T or V, even more preferably T
<220> FEATURE:
<221> NAME/KEY: VARIANT
```

```
<222> LOCATION: (5)..(5)
<223> OTHER INFORMATION: Arbitrary amino acid, preferably P, S, T or F,
      more preferably P or S, even more preferably S

<400> SEQUENCE: 16

Asn Xaa Ser Xaa Xaa
1               5

<210> SEQ ID NO 17
<211> LENGTH: 6
<212> TYPE: PRT
<213> ORGANISM: Hepatitis B virus
<220> FEATURE:
<221> NAME/KEY: VARIANT
<222> LOCATION: (1)..(1)
<223> OTHER INFORMATION: Arbitrary amino acid, preferably D, E or S,
      more preferably D or E, even more preferably D

<400> SEQUENCE: 17

Xaa His Gln Leu Asp Pro
1               5

<210> SEQ ID NO 18
<211> LENGTH: 18
<212> TYPE: PRT
<213> ORGANISM: Hepatitis B virus
<220> FEATURE:
<221> NAME/KEY: VARIANT
<222> LOCATION: (2)..(2)
<223> OTHER INFORMATION: Arbitrary amino acid, preferably L, I or Q,
      more preferably L
<220> FEATURE:
<221> NAME/KEY: VARIANT
<222> LOCATION: (4)..(4)
<223> OTHER INFORMATION: Arbitrary amino acid, preferably T, V, A or is
      not present, more preferably T or V, even more preferably T
<220> FEATURE:
<221> NAME/KEY: VARIANT
<222> LOCATION: (5)..(5)
<223> OTHER INFORMATION: Arbitrary amino acid, preferably P, S, T or F,
      more preferably P or S, even more preferably S
<220> FEATURE:
<221> NAME/KEY: VARIANT
<222> LOCATION: (11)..(11)
<223> OTHER INFORMATION: Arbitrary amino acid, preferably F or L, more
      preferably F
<220> FEATURE:
<221> NAME/KEY: VARIANT
<222> LOCATION: (11)..(11)
<223> OTHER INFORMATION: Arbitrary amino acid, preferably F or L, more
      preferably F
<220> FEATURE:
<221> NAME/KEY: VARIANT
<222> LOCATION: (13)..(13)
<223> OTHER INFORMATION: Arbitrary amino acid, preferably D, E or S,
      more preferably D or E, even more preferably D

<400> SEQUENCE: 18

Asn Xaa Ser Xaa Xaa Asn Pro Leu Gly Phe Xaa Pro Xaa His Gln Leu
1               5                   10                  15

Asp Pro

<210> SEQ ID NO 19
<211> LENGTH: 5
<212> TYPE: PRT
<213> ORGANISM: Hepatitis B virus

<400> SEQUENCE: 19

Gly Cys His Ala Lys
1               5
```

```
<210> SEQ ID NO 20
<211> LENGTH: 8
<212> TYPE: PRT
<213> ORGANISM: Hepatitis B virus

<400> SEQUENCE: 20

Arg Pro Leu Ala Leu Trp Arg Ser
1               5

<210> SEQ ID NO 21
<211> LENGTH: 19
<212> TYPE: PRT
<213> ORGANISM: Hepatitis B virus

<400> SEQUENCE: 21

Lys Asn Leu Ser Thr Ser Asn Pro Leu Gly Phe Phe Pro Asp His Gln
1               5                   10                  15

Leu Asp Pro
```

HYDROPHOBIC MODIFIED PEPTIDES AND THEIR USE FOR LIVER SPECIFIC TARGETING

CROSS-REFERENCE TO RELATED APPLICATIONS

This application is a US National Phase filing of PCT/EP2012/052349, filed on Feb. 10, 2012, which claims priority to U.S. 61/441,492, filed on Feb. 10, 2011. The disclosure therein is expressly incorporated entirely by reference.

The present invention relates to hydrophobic modified peptides derived from preS-domain of hepatitis B virus (HBV) which are versatile vehicles for the specific delivery of compounds to the liver, preferably to hepatocytes, in vitro as well as in vivo. Any kind of compound, in particular drugs can be specifically targeted to the liver and so be enriched in the liver. This liver targeting can further be used for the targeted prevention and/or treatment of liver diseases or disorders, such as hepatitis, malaria, hepatocellular carcinoma (HCC), as well as for the prevention of HAV, HBV, HCV and/or HDV infection. The present invention relates to pharmaceutical compositions comprising said hydrophobic modified peptide(s) and the compound(s) to be specifically delivered to the liver. The present invention furthermore relates to the use of the inventive hydrophobic modified peptides for the prevention and/or treatment of liver diseases or disorders, a method for the prevention and/or treatment of liver diseases or disorders and the use of the hydrophobic modified peptides for the manufacture of a medicament for the prevention and/or treatment of liver diseases or disorders.

BACKGROUND OF THE INVENTION

The liver, an organ which is present in vertebrates and other animals, plays a major role in the metabolism and has a number of functions in the body, including glycogen storage, decomposition of red blood cells, synthesis of plasma proteins, and detoxification. The liver also is the largest gland in the human body. It lies below the diaphragm in the thoracic region of the abdomen. It produces bile, an alkaline compound which aids in digestion, via the emulsification of lipids. It also performs and regulates a wide variety of high-volume biochemical reactions requiring specialized tissues.

Hepatocytes make up 70 to 80% of the cytoplasmic mass of the liver. Hepatocytes are involved in protein synthesis, protein storage and transformation of carbohydrates, synthesis of cholesterol, bile salts and phospholipids, and detoxification, modification and excretion of exogenous and endogenous substances. The hepatocyte also initiates the formation and secretion of bile.

There is a wide number of known liver diseases, such as:
Hepatitis: inflammation of the liver, caused mainly by various viruses but also by certain poisons, autoimmunity or hereditary conditions;
Cirrhosis: the formation of fibrous tissue in the liver, replacing dead liver cells. The death of the liver cells can for example be caused by viral hepatitis, alcoholism or contact with other liver-toxic chemicals;
Haemochromatosis: a hereditary disease causing the accumulation of iron in the body, eventually leading to liver damage;
Cancer of the liver: primary hepatocellular carcinoma (HCC) or cholangiocarcinoma and metastatic cancers, usually from other parts of the gastrointestinal tract;
Wilson's disease: a hereditary disease which causes the body to retain copper;
Primary sclerosing cholangitis: an inflammatory disease of the bile duct, autoimmune in nature;
Primary biliary cirrhosis: autoimmune disease of small bile ducts;
Budd-Chiari syndrome: obstruction of the hepatic vein;
Gilbert's syndrome: a genetic disorder of bilirubin metabolism, found in about 5% of the population;
Glycogen storage disease type II: the build-up of glycogen causes progressive muscle weakness (myopathy) throughout the body and affects various body tissues, particularly in the heart, skeletal muscles, liver and nervous system.

There are also many pediatric liver diseases, such as biliary atresia, alpha-1-antitrypsin deficiency, alagille syndrome, and progressive familial intrahepatic cholestasis; as well as metabolic diseases.

Furthermore, several pathogens and parasites, especially of tropical diseases, have a liver stage during their life cycle. For instance malaria, is one of the most common infectious diseases and an enormous public-health problem. Malaria is caused by protozoan parasites of the genus *Plasmodium*. The most serious forms of the disease are caused by *Plasmodium falciparum* and *Plasmodium vivax*, but other related species (*Plasmodium ovale, Plasmodium malariae*, and sometimes *Plasmodium knowlesi*) can also infect humans. This group of human-pathogenic *Plasmodium* species is usually referred to as malaria parasites. Malaria parasites are transmitted by female *Anopheles* mosquitoes. Malaria in humans develops via two phases: an exoerythrocytic (hepatic phase or "liver stage") and an erythrocytic phase. When an infected mosquito pierces a person's skin to take a blood meal, sporozoites in the mosquito's saliva enter the bloodstream and migrate to the liver. Within about 30 minutes of being introduced into the human host, they infect hepatocytes, multiplying asexually and asymptomatically for a period of 6-15 days. Once in the liver these organisms differentiate to yield thousands of merozoites which, following rupture of their host cells, escape into the blood and infect red blood cells, thus beginning the erythrocytic stage of the life cycle. The parasite escapes from the liver undetected by wrapping itself in the cell membrane of the infected host liver cell. The parasite is relatively protected from attack by the body's immune system because for most of its human life cycle it resides within the liver and blood cells and is relatively invisible to immune surveillance. There is increasing interest in developing drugs that specifically address the liver specific stages of malaria parasites (e.g. primaquine, gyrase inhibitors like levofloxacin, doxorubicin) in order to obviate the development of blood stages.

Another example is schistosomiasis or bilharziosis, which is a parasitic disease caused by several species of flatworm. Although it has a low mortality rate, schistosomiasis can be very debilitating. It is an often chronic illness that results from infection of the blood with a parasitic flatworm (schistosome). It causes debilitation and causes liver and intestinal damage. It is most commonly found in Asia, Africa, and South America, especially in areas with water that is contaminated with fresh water snails, which contain the parasite.

Hepatitis B virus (HBV), the cause for hepatitis B, is the prototype of a family of small, enveloped DNA viruses of mammals and birds (1). The HBV envelope encloses three proteins termed L-(large), M-(middle) and S-(small) (see FIG. 1). They share the C-terminal S-domain with four transmembrane regions. The M- and L-protein carry additional N-terminal extensions of 55 and, genotype-dependent, 107 or 118 aa (preS2- and preS1). In virions the stoichiometric ratio of L, M and S is about 1:1:4, while the more abundantly secreted non-infectious subviral particles (SVPs) contain almost exclusively S- and only traces of L-protein (2). During synthesis, the preS1-domain of L is myristoylated and at some point of the HBV life cycle translocated through the ER-derived membrane. This modification is essential for infectivity (3,4). A pronounced feature of HBV is its liver tropism, i.e. the liver is the tissue which specifically supports the growth of HBV.

Ideally, drug targeting should fulfil the following criteria: 1) exclusive transfer of the drug to the required site of action; 2) a minimum of effects for the remaining organism; 3) use of a pharmacologically inactive vector.

In order to carry a drug i.e. a therapeutic active agent to a specific tissue, different strategies are pursued. These are for example the use of prodrugs, from which the pharmacologically active part is released in the target tissue by tissue-specific enzymes. A further possibility is to couple effective, non-tissue-specific drugs to tissue-specific, but pharmacologically inert carrier systems like receptor-affine peptides or colloidal particles.

Various drug carriers have been used to enhance liver targeting of drugs. A straightforward approach is based on the active phagocytosis of the reticuloendothelial system in the liver by delivering drugs in particular carriers, such as liposomes and microspheres. For example, it has been shown that following i.v. (intravenous) injection, particulate carriers incorporating a drug are mainly captured by the reticuloendothelial system in the liver, resulting in drug targeting of the liver (5). On the other hand, liver targeting of drugs with positively charged, water-soluble polymers is based on free extravasation of most water-soluble substances from the vascular system of the liver as well as on negative charges on the liver cell surface (6). Thus, polymers have been used as the carrier to allow drugs to target to the liver based on such anatomical and biochemical characteristics of the liver. More specific drug targeting of the liver has been attempted by using asialoglycoprotein receptors of liver cells. The asialoglycoprotein receptor (galactose receptor) is present on hepatocytes with high density. In addition, once a ligand binds to the galactose receptor, the ligand-receptor complex is internalized which allows the cellular uptake of galactosylated ligands (7). Furthermore delivery approaches using nanoparticles have been performed by e.g. amphilic polymers and viral vectors (8). Also delivery of drugs and genetic material has been conducted via the use of bio-nanocapsules (BNCs). BNCs are described as "nanoscaled capsules consisting of proteins produced by biotechnological techniques" and can be used as delivery systems for organ specific drug delivery (9).

U.S. Pat. No. 7,001,760 B2 disclose recombinant vectors derived from hepatitis B virus (HBV), which can be used for gene therapy, such as the delivery of therapeutic genes to liver cells and the expression of heterologous genes in liver cells.

WO2009/092612, whose content is incorporated herewith by reference in its entirety, describes hydrophobic modified preS-derived peptides of HBV and their use as vehicles for the specific delivery of compounds to the liver. In this document, the hydrophobic modified preS-derived peptides of HBV may be coupled with a diagnostic or therapeutic active agent via an optional anchor group (A) which is preferably "C-terminal" of the hydrophobic modified preS-derived peptide.

The present invention provides hydrophobic modified peptides conjugated to one ore more compounds, preferably being drug(s), which compounds are coupled to the N-terminal amino acid sequence of the peptide represented by X, making it possible to create shorter peptides while still maintaining liver specificity. Surprisingly it has become possible to couple hydrophobic moieties to the peptides without abrogating liver tropism. The coupling compounds like drugs to the N-terminal site allows better delivery of active compounds across the cell membrane and also allows to direct drugs, which are active on the cellular membrane, directly to the site of action. Furthermore, the coupling of a drug to the N-terminal region of the peptide contributes to the stability of this active substance. In FIG. 3, the molecular mechanism of the binding of a hydrophobic modified peptide to the surface of a hepatocyte is schematically illustrated.

SUMMARY OF THE INVENTION

According to the present invention this object is solved by providing a hydrophobic modified peptide. In FIG. 2, the construction of a hydrophobic modified peptide of the invention is schematically illustrated. Said hydrophobic modified peptide has the general formula: $[X-P-Y-R_o] A_p$ wherein P is a peptide having the amino acid sequence NPLGFXaaP (SEQ ID NO:1) (single-letter code; wherein Xaa is an arbitrary amino acid, preferably F or L, more preferably F). X is an amino acid sequence having a length of m amino acids, wherein one or more of the amino acids of X carry one or more group for hydrophobic modification selected from acylation, preferably with carboxylic acids, saturated and unsaturated fatty acids, C 8 to C 22 fatty acids, amino acids with lipophilic side chains, and addition of hydrophobic moieties selected from cholesterol, derivatives of cholesterol, phospholipids, glycolipids, glycerol esters, steroids, ceramids, isoprene derivatives, adamantane, farnesol, aliphatic groups, polyaromatic compounds and m is at least 4 (m is ≥4).

In a preferred embodiment the hydrophobic modification is effected by acylation with acyl moieties preferably selected from myristoyl (C 14), palmitoyl (C 16) or stearoyl (C 18), more preferably by acylation with myristoyl (C 14) or by acylation with stearoyl (C 18). Y is an amino acid sequence having a length of n amino acids, (n is 0 or at least 1). In the above general formula m+n are at least 11, that is, the hydrophobic modified peptide of the invention has a length of at least 18 amino acids (aa) in total. R is a C-terminal modification of said hydrophobic modified peptide, which is preferably a moiety that protects from degradation selected from amide, D-amino acid, modified amino acid, cyclic amino acid, albumin, natural and synthetic polymer, such as PEG, glycane (o is 0 or at least 1). A is an anchor group, preferably selected from ester, ether, disulfide, amide, thiol, thioester, p is 0 or at least 1. In a preferred embodiment m is 4 to 19 and/or n is 0 to 78. One or more compound(s), preferably one or more drug(s) is/are coupled to one or more of the amino acid(s) of X. The compound may be composed of one substance or may comprise two or more substances, which are linked together by any kind of chemical or physical bond, like covalent bond, ionic bond etc. or which is in the form of a complex.

In a preferred embodiment of the invention, the one or more compound(s) is/are linked to said peptide via a linker or spacer, wherein the linker or spacer is preferably cleaved off the conjugate with the hydrophobic modified peptide by a liver protein, preferably a hepatocellular proteolytic enzyme which may be selected from cytochromes, such as cytochrome P450, proteases and lyases of the endocytic pathway (e.g. esterases), matrix-metallo-proteases MMP1, MMP2, MMP7, MMP9 and MMP12, preferably MMP7. In this case, the linker or spacer preferably comprises the peptide sequences GCHAK (SEQ IDNO:19) or RPLALWRS (SEQ ID NO:20).

In a further preferred embodiment, the one or more drug(s) is/are coupled to one or amino acid(s) of X having an amino group in a side chain, which is/are preferably selected from lysine, α-amino glycine, α,γ-diaminobutyric acid, ornithine, α,β-diaminopropionic acid, more preferably lysine. The amino acid(s) having an amino group in a side chain is/are preferably located at the N-terminus of X, wherein preferably 1 to 11, more preferably 1 to 3, amino acids having an amino group in a side chain are located at the N-terminus of X.

According to the present invention this object is furthermore solved by providing a pharmaceutical composition comprising at least one hydrophobic modified peptide as defined herein and at least a compound (e.g. a drug) to be specifically delivered to the liver, preferably to hepatocytes, as defined herein and optionally a pharmaceutically acceptable carrier and/or excipient. In a preferred embodiment, the hydrophobic modified peptide and the pharmaceutical composition are used in the specific delivery of drugs to the liver, preferably for use in the treatment and prevention of a liver disease or disorder.

In a preferred embodiment, the compound is a cell-penetrating peptide (CPP).

In a preferred embodiment, combinations of two or more different compounds are coupled to one hydrophobic modified peptide. More preferably, the one or more compound which is/are coupled or linked to one or amino acid(s) of X is one or more drug or a combination of two or more drugs.

According to the present invention the object is furthermore solved by providing a use of the hydrophobic modified peptide or the pharmaceutical composition of the invention for the manufacture of a medicament for prevention and/or treatment of liver diseases or disorders.

According to the present invention the object is furthermore solved by providing a method for prevention and/or treatment of liver diseases or disorders, comprising administering to a subject a therapeutically effective amount of a hydrophobic modified peptide or a pharmaceutical composition of the invention.

Further preferred embodiments of the present invention are defined in the dependent claims.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Hydrophobic Modified Peptides

As outlined above, the present invention provides hydrophobic modified peptides which are derived from the preS domain of hepatitis B virus (HBV) (also designated "preS-peptides"). The envelope of HBV encloses three proteins termed L (large), M (middle) and S (small) (see FIG. 1). They share the C-terminal S-domain with four transmembrane regions. The M- and L-protein carry additional N-terminal extensions of 55 and, genotype-dependent, 107 or 118 amino acids (preS2- and preS1).

Thus, the peptide according to the present invention refers to a peptide with an amino acid sequence that corresponds to or is based on the N-terminal extensions of the L-protein of HBV, preS1, preferably of genotypes A to H as well as of woolly monkey (WMHBV), orangutan, chimpanzee and gorilla hepatitis B viruses, but it also refers to variants thereof, preferably C-terminally truncated variants, amino acid substitution variants. As an indispensible sequence, the amino acid residues being important for the liver tropism of the hydrophobic modified preS-derived peptides of HBV, as set out in SEQ ID NO:1 (NPLGFXP) are present in the amino acid sequence of the hydrophobic modified peptide of the invention. In particular, the hydrophobic modified peptides of the invention are based on the following sequences (amino acids in single letter code; essential domain underlined).

Essential domain of the hydrophobic modified peptide (SEQ ID NO:1):

NPLGFXP (wherein X is an arbitrary amino acid, preferably F or L, more preferably F)

```
preS HBV-A (ID: M57663; SEQ ID NO: 2):
MGGWSSKPRKGMGTNLSVPNPLGFFPDHQLDPAFGANSNNPDWDFNPIKD

HWPQANQVGVGAFGPGFTPPHGGVLGWSPQAQGILATVPAMPPPASTNRQ

SGRQPTPISPPLRDSHPQA preS HBV-B (ID: D00329, SEQ ID NO: 3)
MGGWSSKPRKGMGTNLSVPNPLGFFPDHQLDPAFKANSENPDWDLNPHKD

NWPDAHKVGVGAFGPGFTPPHGGLLGWSPQAQGILTSVPAAPPPASTNRQ

SGRQPTPLSPPLRDTHPQA preS HBV-C (ID: AB048704, SEQ ID NO: 4)
MGGWSSKPRKGMGTNLSVPNPLGFFPDHQLDPAFKANSENPDWDLNPHKD

NWPDAHKVGVGAFGPGFTPPHGGLLGWSPQAQGILTSVPAAPPPASTNRQ

SGRQPTPLSPPLRDTHPQA preS HBV-Chimpanzee (ID: AB032432, SEQ ID NO: 5)
MGQNLSTSNPLGFFPEHQLDPAFKANTNNPDWDFNPKKDYWPEANKVGAG

AFGPGFTPPHGGLLGWSPQAQGILTTLPANPPPASTNRQSGRQPTPLSPP

LRDTHPQA preS HBV-D(ID: AB048702, SEQ ID NO: 6)
MGQNLSTSNPLGFFPDHQLDPAFRANTNNPDWDFNPNKDTWPDANKVGAG

AFGLGFTPPHGGLLGWSPQAQGIMQTLPANPPPASTNRQSGRQPTPLSPP

LRTTHPQA
```

-continued preS HBV-E (ID: X65657, SEQ ID NO: 7)
MGLSWTVPLEWGKNISTT<u>NPLGFFP</u>DHQLDPAFRANTRNPDWDHNPNKDH

WTEANKVGVGAFGPGFTPPHGGLLGWSPQAQGMLKTLPADPPPASTNRQS

GRQPTPITPPLRDTHPQA preS HBV-F (ID: X69798@8, SEQ ID NO: 8)
MGAPLSTTRRGMGQNLSVP<u>NPLGFFP</u>DHQLDPLFRANSSSPDWDFNTNKD

SWPMANKVGVGGYGPGFTPPHGGLLGWSPQAQGVLTTLPADPPPASTNRR

SGRKPTPVSPPLRDTHPQA preS HBV-G (ID: AF160501, SEQ ID NO: 9)
MGLSWTVPLEWGKNLSAS<u>NPLGFLP</u>DHQLDPAFRANTNNPDWDFNPKKDP

WPEANKVGVGAYGPGFTPPHGGLLGWSPQSQGTLTTLPADPPPASTNRQS

GRQPTPISPPLRDSHPQA

HBV Gibbon (ID: AJ131572, SEQ ID NO: 10)
MGQNHSVT<u>NPLGFFP</u>DHQLDPLFRANSNNPDWDFNPNKDTWPEATKVGVG

AFGPGFTPPHGGLLGWSPQAQGILTTLPAAPPPASTNRQSGRKATPISPP

LRDTHPQA

HBV-H (ID: Q8JMY6, SEQ ID NO: 11)
MGAPLSTARRGMGQNLSVP<u>NPLGFFP</u>DHQLDPLFRANSSSPDWDFNTNKD

NWPMANKVGVGGFGPGFTPPHGGLLGWSPQAQGILTTSPPDPPPASTNRR

SGRKPTPVSPPLRDTHPQA

HBV Orangutan (ID: AF193864, SEQ ID NO: 12)
MGQNLSVS<u>NPLGFFP</u>EHQLDPLFRANTNNPDWDFNPNKDTWPEATKVGVG

AFGPGFTPPHGGLLGWSPQAQGVTTILPAVPPPASTNRQSGRQPTPISPP

LRDTHPQA

HBV Woolly Monkey (ID: NC_001896, SEQ ID NO: 13)
MGLNQSTF<u>NPLGFFP</u>SHQLDPLFKANAGSADWDKNPNKDPWPQAHDTAVG

AFGPGLVPPHGGLLGWSSQAQGLSVTVPDTPPPPSTNRDKGRKPTPATPP

LRDTHPQA

"Variants" are preferably N-terminally and/or C-terminally truncated variants, amino acid substitution or deletion variants, or prolonged variants of the sequences of SEQ ID NOs: 2-13, carrying a hydrophobic modification and wherein one or more drug(s) is/are coupled to one or amino acid(s) N-terminal of the essential domain of the hydrophobic modified peptide. Variants comprise furthermore an amino acid sequence comprising modified amino acid(s), unnatural amino acid(s) or peptidomimetic(s) or further compounds which can mimic a peptide backbone/structure. Preferably, variants are selected from C-terminally truncated variants of SEQ ID NOs. 2 to 13; amino acid substitution or deletion variants; variants comprising modified amino acid(s), unnatural amino acid(s) or peptidomimetic(s) or further compounds which can mimic a peptide backbone/structure.

According to the invention, a variant of a hydrophobic modified peptide comprise at least the amino acids having the sequence of SEQ ID NO: 1 and can consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 or 119 amino acids of the above SEQ ID NOs: 2 to 13, or variants thereof.

N-terminally and/or C-terminally truncated variants comprise preferably at least 18 consecutive amino acids, more preferably at least 19 consecutive amino acids, even more preferably at least 20 and just even more preferably at least 21 consecutive amino acids of SEQ ID NOs. 2 to 13 or variants thereof.

The N-terminal sequence (X) of the hydrophobic modified peptide having a length of m amino acids comprises at least 4 amino acids (i.e. m=4). Preferably, the N-terminal sequence (X) of the hydrophobic modified peptide can consist of 4, 5, 6, 7, 8, 9, 10, 11, 12, 13, 14, 15, 16, 17, 18, or 19 amino acids. That is, m may be 4 to 19.

In a preferred embodiment, one or amino acid(s) of X have an amino group in a side chain, which is/are preferably selected from lysine, α-amino glycine, α,γ-diaminobutyric acid, ornithine, α,β-diaminopropionic acid, more preferably lysine. The amino acid(s) of X having an amino group in a side chain, is/are preferably is/are located at the N-terminus of X, wherein one to eleven (1-11), preferably one to three (1-3), amino acids having an amino group in a side chain are located at the N-terminus of X.

In a preferred embodiment, the N-terminal sequence (X) of the hydrophobic modified peptide preferably comprises the sequence $NX_1SX_2X_3$ (SEQ ID NO: 16), wherein $X_1$, $X_2$ and, $X_3$ may be arbitrary amino acids. Preferably, $X_1$ of SEQ ID NO: 16 is L, I or Q, more preferably L. Preferably, $X_2$ of SEQ ID NO: 16 is T, V, A or is not present, preferably T or V, more preferably T. Preferably, $X_3$ of SEQ ID NO: 16 is P, S, T or F, more preferably P or S, even more preferably S. Preferably, the sequence $NX_1SX_2X_3$ (SEQ ID NO: 16) is directly attached to the N-terminus of the peptide P (SEQ. ID NO: 1; NPLGFXaaP), resulting in a peptide comprising the sequence $NX_1SX_2X_3NPLGFXaaP$, wherein $X_1$, $X_2$, $X_3$ and Xaa are defined as above.

The C-terminal sequence (Y) of the hydrophobic modified peptide having a length of n amino acids comprises 0 or at least 1 amino acids (i.e. n≥0). Preferably, the C-terminal sequence (Y) of the hydrophobic modified peptide can consist of 0, 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92 or 93 amino acids. That is, n may be 0 to 93.

In a preferred embodiment, the C-terminal sequence (Y) of the hydrophobic modified peptide consists of at least 4 amino acids (n=4), which preferably has the sequence $X_4HQLDP$ (SEQ ID NO: 17), wherein $X_4$ is an arbitrary amino acid. Preferably, $X_4$ of SEQ ID NO: 17 is D, E or S, more preferably D or E, even more preferably D. Preferably, the sequence $X_4HQLDP$ (SEQ ID NO: 17) is directly attached to the C-terminus of the peptide P (SEQ. ID NO: 1; NPLGFXaaP), resulting in a peptide comprising the sequence $NPLGFXaaPX_4HQLDP$, wherein $X_4$ and Xaa are defined as above.

In a preferred embodiment, the hydrophobic modified peptide of the present invention comprises a peptide encoded by the amino acid sequence $NX_1SX_2X_3NPLGFXaaPX_4HQLDP$ (SEQ ID NO: 18), wherein $X_1$, $X_2$, $X_3$, $X_4$ and Xaa are defined as above.

The term "variant" also refers to the homologous sequences found in the different viral species, strains or subtypes of the hepadnavirus genus, such as HBV strain alpha, HBV strain LSH (chimpanzee isolate), woolly monkey HBV (WMHBV), or strains selected from the group consisting of the HBV genotypes A to H (see SEQ ID NO: 2-13).

The term "variant" also refers to homologous sequences which show at least 50% sequence identity to an amino acid sequence comprising the invariant NPLGFXaaP-domain and the adjacent sequences of SEQ ID NO. 2-13 or any other amino acid sequence disclosed herein, preferably 70%, more preferably 80%, even more preferably 90% or 95%.

Thus, a preferred hydrophobic modified peptide according to the invention comprises a variant of SEQ ID NOs. 2 to 13 with an amino acid sequence of the different viral species, strains or subtypes, preferably of the genotypes of HBV or woolly monkey HBV (WMHBV) or variants thereof.

"Variants" of SEQ ID NOS. 2 to 13 also comprise variants or "analogues" comprising amino acid deletions, amino acid substitutions, such as conservative or non conservative replacement by other amino acids or by isosteres (modified amino acids that bear close structural and spatial similarity to protein amino acids), amino acid additions or isostere additions, as long as the sequence still shows liver tropism, preferably more than 10% of the injected dose accumulates in liver tissue after 1 h following intravenous injection. The liver tropism of the of the hydrophobic modified peptide or of its "variant" is preferably 10% or more of the injected dose after 1 h, more preferred 25% or more of the injected dose after 1 h, even more preferred 50% or more of the injected dose after 1 h.

Conservative amino acid substitutions typically relate to substitutions among amino acids of the same class. These classes include, for example, amino acids having uncharged polar side chains, such as asparagine, glutamine, serine, threonine and tyrosine;
  amino acids having basic side chains, such as lysine, arginine, and histidine;
  amino acids having acidic side chains, such as aspartic acid and glutamic acid; and
  amino acids having nonpolar side chains, such as glycine, alanine, valine, leucine, isoleucine, proline, phenylalanine, methionine, tryptophan, and cysteine.

"N-terminal" refers to the N-terminus of X, i.e. the respective first amino acid residue, but comprises also the hydrophobic modification in close proximity to the N-terminus, such as respective amino acid residues (−4), (−3), (−2), (−1), 1, 2 or 3 or 4. Thus, the coupling of the compound (e.g. a drug) and the hydrophobic modification can furthermore be obtained by an attachment of a drug and a hydrophobic moiety at a site close to the N-terminus of X.

The hydrophobic modification of said hydrophobic modified peptide according to the present invention adds a hydrophobic moiety to the peptide.

X is modified with at least one hydrophobic moiety or group. In preferred embodiments of this invention, X is modified with 1, 2, 3, 4 or more hydrophobic moiety/ies or group(s). That is, X can be modified with more than one hydrophobic moiety or group, such as 2. The hydrophobic moieties or groups can be the same or different to each other. The hydrophobic modification of said peptide according to the present invention is selected from:
  acylation;
  addition of hydrophobic moieties.

Acylation is preferably selected from acylation with carboxylic acids, fatty acids, amino acids with lipophilic side chains. Preferred fatty acids are saturated or unsaturated fatty acids, branched or unbranched fatty acids, preferably with 8 to 22 carbon atoms (C 8 to C 22). More preferably, the hydrophobic modification by acylation is selected from acylation with myristoyl (C 14), palmitoyl (C 16) or stearoyl (C 18). Modification by myristoylation is preferred in in vivo and medicinal applications due to its higher safety, e.g. not showing the adverse effects of the stearoyl group (innate immune response etc). The addition of hydrophobic moieties is preferably selected from addition of cholesterol, derivatives of cholesterol, phospholipids, glycolipids, glycerol esters, steroids, ceramids, isoprene derivatives, adamantane, farnesol, aliphatic groups, polyaromatic compounds. The attachment of the hydrophobic moieties is preferably by covalent binding, which can be achieved via carbamate, amide, ether, disulfide or any other linkage that is within the skill of the person skilled in the art. Thus, the hydrophobic modified, preferably acylated peptides of this invention are preferably lipopeptides due to their N-terminal lipophilic or hydrophobic group/moiety.

The C-terminal modification (R) of Y is preferably a modification with a moiety that protects from degradation, such as in vivo degradation.

"C-terminal" refers to the modification at the C-terminus, i.e. the respective last amino acid residue, but comprises also the modification in close proximity to the C-terminus, such as the last but one amino acid residue, the last but two amino acid residue or more amino acid residues (e.g. introduction of one D-amino acid that protects the carrier from enzymatic degradation e.g. by the action of carboxypeptidases). The skilled artisan will be able to select the respective suitable moiety(s) depending on the respective application. Preferred moieties that protect from degradation are selected from amides, D-amino acids, modified amino acids, cyclic amino acids, albumin, natural and synthetic polymers, such as PEG, glycane.

Furthermore, o is 0 or at least 1, i.e. the C-terminal modification (R) is optional. Preferably, o is 1. In further embodiments of this invention o is 1, 2, 3, 4 or more. That is, the C-terminus of hydrophobic modified peptide or its proximity can be modified with more than one moiety or group, such as 2. The moieties or groups can be the same or different to each other. In an embodiment of this invention the hydrophobic modification and/or R are linked to the peptide via a linker or spacer. Linker or spacer are known to the skilled artisan, such as polyalanine, polyglycin, carbohydrates, (CHa)n groups. The skilled artisan will, thus, be able to select the respective suitable linker(s) or spacer(s) depending on the respective application.

The optional anchor group (A) serves as an additional point of attachment for a compound, a tag, a label and is located at an amino acid of Y. That is, in case that at least one anchor group (A) is present (i.e. p≥1) Y comprises at least one amino acid, too (i.e. n≥1). In a preferred embodiment, the anchor group is "C-terminal" of Y, wherein "C-terminal" refers to the modification at the C-terminus, i.e. the respective last amino acid residue, but comprises also the close proximity of the C-terminus, such as the last but one amino acid residue, the last but two amino acid residue or more amino acid residues. In this case o can be 0, thus there is no other C-terminal modification R. The anchor group A can be at an amino acid side chain of Y or can be the amino acid side chain of Y itself, i.e. A can be a side chain itself or a modified side chain. The anchor group can also be a modified amino acid residue which was introduced into the amino acid sequence of Y to serve as an anchor group. In other embodiments of the invention the anchor group A is attached to the hydrophobic modification of X and/or the C-terminal modification R. Preferred anchor groups are selected from ester, ether, disulfide, amide, thiol, thioester. The skilled artisan will be able to select the respective suitable anchor group(s) depending on the respective compound, tag, label etc. to be attached. The anchor group can furthermore be suitable for attaching a complex-forming component, such as of the biotin/avidin, polyarginine/oligonucleotide (e.g. siRNA) complex. Furthermore, o is 0 or at least 1, i.e. the anchor group (A) is optional. Preferably, o is 1. In further embodiments of this invention o is 1, 2, 3, 4 or more. That is, there are more than one anchor group, such as 2. The anchor groups can be the same or different to each other, allowing the attachment of several compounds, such as a drug and a label or different drugs.

Synthesis of the Hydrophobic Modified Peptides

The peptides of the invention can be prepared by a variety of procedures readily known to those skilled in the art, in general by synthetic chemical procedures and/or genetic engineering procedures. Synthetic chemical procedures include more particularly the solid phase sequential and block synthesis (Erickson and Merrifield, 1976). More details can be taken from WO2009/092612.

The solid phase sequential procedure can be performed using established automated methods such as by use of an automated peptide synthesizer. In this procedure an [alpha]-amino protected amino acid is bound to a resin support. The resin support employed can be any suitable resin conventionally employed in the art for the solid phase preparation of (poly)peptides, preferably polystyrene which has been copolymerized with polyoxyethylen to provide sites for ester formation with the initially introduced o-amino protected amino acid. This optimized method, applied by the inventors, has been explicitly described (see e.g. 12). The amino acids are introduced one by one (stepwise). Each synthesis cycle corresponding to the introduction of one amino acid includes a deprotection step, successive washing steps, a coupling step with activation of the amino acid, and subsequent washing steps. Each of these steps is followed by a filtration. The reactive agents for coupling are the classical reactive agents for (poly)peptide synthesis such as dicyclohexylcarbodiimide, hydroxybenzotriazole, benzotriazil-1-yl-oxytris (dimethylamino) phosphonium hexafluorophosphate, and diphenylphosphorylazide. After synthesis of the polypeptide on the resin, the polypeptide is separated from the resin by a treatment with a strong acid such as trifluoroacetic acid in the presence of anisol, ethanedithiol or 2-methylindole. The compound is then purified by the classical techniques of purification, in particular by means of HPLC.

The peptides of the present invention may also be obtained by coupling (poly)peptide fragments that are selectively protected, this coupling being effected e.g. in a solution. The peptides can further be produced by genetic engineering techniques as known to the skilled artisan. A eukaryotic expression system, such as the baculovirus system, is particularly suitable. According to this procedure proteins are expressed in insect cells infected with a recombinant baculovirus containing a nucleic acid sequence encoding a heterologous protein and regulating nucleic acid sequences, such as a promoter. Several cell-lines are available for infection with recombinant baculovirus, such as cell line Sf-9, available from the American Type Culture Collection (CRL 1711). Expression in prokaryotic expression system, such as E. coli, is also particularly suitable.

The introduction of the hydrophobic moiety to the peptide can be accomplished by a variety of procedures readily known to those skilled in the art, including synthetic and genetic engineering approaches.

Alternatively, the peptides and/or fusion peptides (i.e. hydrophobic modified peptides) can be produced by stably transfected eukaryotic cell lines, like CHO and other cell lines which are known in the art and usually used for generating vaccines and the like. Due to the intrinsic property that the N-terminal 47-preS1 amino acids promote secretion of a myristoylated protein/peptide, the biologically active hydrophobic modified peptide can be extracted from cell culture supernatants.

Vectors and Shuttles for Liver Targeting

As outlined above, the present invention provides the use of the hydrophobic modified peptides as vehicle or shuttle for the specific delivery of a compound (e.g. a drug) to the liver, wherein the drug is coupled to the hydrophobic modified peptides as described herein.

"Vehicle" or "shuttle" for the specific delivery of a compound to the liver according to the present invention refers to the liver tropism or hepatotropism of the hydrophobic modified peptides as found by the inventors and described herein, i.e. to their capacity to selectively accumulate in the liver, preferably to selectively accumulate at the plasma membrane of hepatocytes as well as to selectively enter into hepatocytes. The invention is based on the finding of a highly specific liver accumulation and on the identification of the determinants of the liver tropism of HBV in the preS 1 sequence of HBV by the inventors. Thus, the invention uses the knowledge about the determinants of the liver tropism for the design of universal vehicles or shuttles for specific liver targeting or delivery, respectively. The hydrophobic modified peptides of the present invention are versatile vehicles or shuttles for specifically delivering compound(s) to the liver.

Preferably, the specific delivery of a compound to the liver is the specific delivery of the compound to hepatocytes. Furthermore, the compound can specifically be delivered to hepatocytes in vitro as well as in vivo. The compound is preferably specifically delivered to the liver of an animal, preferably mammal or human, or a bird.

Compounds to be Delivered

The compounds (e.g. drugs) to be specifically delivered to the liver according to this invention can be any kind of compound, being preferably suitable for therapeutic purposes.

Drugs can be in form of prodrugs or preprodrugs. A compound can also be a virus or derivatives thereof, such as a replication-deficient or a replication-competent recombinant virus (e.g. an Adenovirus or an Adeno-associated virus) that has been chemically or genetically modified to expose the targeting sequence on its surface and is thereby redirected to infect hepatocytes. These viruses shall be applicable for hepatocyte specific gene delivery.

Drug (Therapeutic Agent)

In a preferred embodiment of the invention the compound to be specifically delivered to hepatocytes is a drug (or a drug in form of a prodrug). This drug/prodrug is preferably selected from therapeutically active compounds, drugs, agents, more preferably from the following classes of substances:

Radioactive molecules or isotopes (e.g. $^{18}$F, $^{51}$Cr, $^{67}$Ga, $^{68}$Ga, $^{111}$In, $^{99m}$Tc), alkylating agents (e.g cisplatin, oxalplatin), anti-metabolites (e.g. azathioprine), anti-neoplastics (e.g. bleomycine, actinomycine) anthracyclines (e.g. doxorubicin, epirubicin), antifolates, (e.g. Methotrexate) antiviral agents (e.g. ribavarin, tenofovir), cytoskeleton-disrupting drugs (e.g. vinblastine, TAXOL), cytokines (e.g. interferon-α, interferon-β), chemokines (e.g CCL1, CXC1), siRNAs (e.g CALAA-01, SIRNA-034), miRNAs (e.g. miR-26a), nuclear receptor agonists and antagonists (e.g. mifepristone), oligonucleotides and nucleic acids (e.g. plasmids, short dsDNA, short ssDNA), epothilone (e.g. patupilone, ixabepilone), hormones (e.g., progestrines, fluoxymesterone), hormone antagonists (e.g. toremifene, fulvestrant), immunosuppressive agents (e.g. rapamycine, cyclosporine A), immunomodulatory agents (e.g. lenalidomide), immune stimulatory agents (e.g. SDC101, ITMN-191), immune stimulatory sequences such as TLR agonists, kinase inhibitors (e.g. sorafenib, imatinib, erlotinib), protease inhibitors (e.g. boceprevir, telaprevir), polymerase inhibitors (e.g. MK-0608, R7128), topoisomerase inhibitors (e.g. irinotecan, topotecan), nucleoside analogues (e.g. telbivudine, entecavir), precursor analogues (e.g. fluorouracil), peptides and peptide antibiotics (e.g. defensin 1), antibiotics (e.g. azithromycin, clindamycin, rifampicin), gyrase inhibitors of the fluoroquinilone class (e.g. levofloxacin, clinafloxacin, gatifloxacin, gemifloxacin, moxifloxacin, sitafloxacin, trovafloxacin, prulifloxacin, garenoxacin, delafloxacin), platin-based agents (e.g. carboplatin, cisplatin), retinoids (e.g. tazarotene, bexarotene), vinca alkaloids (e.g. vinpocetine, vinorelbine) and their derivatives, cytotoxic agents and cytostatic agents like ribosome inactivating proteins (e.g. a-sarcin, restrictotin), vitamins (e.g. vitamin B6), $\alpha$-chain toxins (e.g. diphtheria toxin,), snake venom toxins and their components (e.g. cobratoxin), fungi derived agents (e.g. aspergillin), bacterial exotoxins (e.g., *Pseudomonas* exotoxin), bacterial enterotoxins (e.g. cholera toxin) and bacterial endotoxins (e.g. lipopolysaccharide) and their analogues, antibodies (e.g. bevacizumab, cetuximab) and CADs (cationic amphilic drugs) such as prochlorperazine, fluphenazine, trifluorophenazine.

Preferred embodiments of the invention may include one or more member of the above classes of substances, in particular dapsone, bleomycin, dactinomycin, mitomycin, daunorubicin, doxorubicin, cyclosporin A, tenofovir, lamivudine, adefovir, entecavir, ribavirin, telepravir, epirubicin, idarubicin, mitoxantrone, amsacrin, doxifluridine, cisplatin, carboplatin, oxaliplatin, satraplatin, camptothecin, topotecan, irinotecan, amsacrine, etoposide, teniposide, cyclophosphamide, ifosfamide, trofosfamide, melphalan, chlorambucil, estramustin, busulfan, chlormethine, treosulfan, carmustine, lomustine, nimustine, streptozocin, procarbazine, dacarbazine, temozolomide, thiotepa, vinorelbine, vincristine, vinblastine, vindesine, paclitaxel, docetaxel, methotrexate, pemetrexed, raltitrexed, fluorouracil, capecitabine, cytosine-arabinoside, gemcitabine, tioguanine, pentostatin, azathioprine, mercaptopurine, fludarabin, cladribine, hydroxycarbamide, mitotane, azacitidine, cytarabine, gemcitabine, nelarabine, bortezomib, anagrelide, preferably imatinib, erlotinib, sunitinib, sorafenib, dasatinib, lapatinib or nilotinib, MK 886, pizotlyene, toremifene, SDC-101, ITMN-191, RG7227, nitazoxanide, VX-950, VX-222, BMS-790052, BMS-650032, GS 9190, GS 9256, BI 201335, BI 207127, IDX184, R7128, boceprevir, MK-7009, SIRNA-034, MK-0608, R7128, RG7347, RG7348, TMC435, PF-868554, PF-4878691, TT033, BI201335, BI 207127, BMS-790052, BMS-791325, BMS-650032, BMS-824393, ANA598, VCH-759, G1 50005, ITX5061, ITX4520, IDX184, IDX320, IDX375, A-837093, GS 9190, GS 9256, ACH-1095, ACH-1625, PPI-461, PPI1301, TG4040, AZD7295, chemizole, SPC3649, GNI-104, ID-12, GSK625433, ABT-450, ABT-072, ABT-333, PSO-7977, INX09189, PSI-938, EDP-239, SDC-101, SP-30, AVL-181, VX-500 and combinations thereof.

In a preferred embodiment, the drug is selected from the group consisting of primaquine, doxorubicin and gyrase inhibitors, preferably levofloxacin.

Doxorubicin is used as a first line drug for the treatment of primary HCC and has been found to act as an anti-malaria drug (Friedman R, (2009); 38; Gamo F J et al. (2010); 39). However, doxorubicin displays severe cardiotoxicity and nephrotoxicity. Coupling of doxorubicin to the hydrophobic modified peptides of the invention eliminates the target toxicity of this drug.

Gyrase inhibitors of the fluoroquinilone class like levofloxacin are known to inhibit liver stage malaria (Friesen et al., Scie. Transl. Med., 2010; 40). To be effective as an anti-malarai drug, long time daily use is required. Further, gyrase inhibitors are known to develop intolerance if high dosage, long term use is required. Coupling of gyrase inhibitors like levofloxacin can reduce high dosage use and allow depot induction using subcutaneous injection.

The above specified drugs may be used alone or in any suitable combination with each other. Preferred combinations for the treatment of unresectable hepatocellular carcinoma are combinations of bortezumib and doxorubicin; sorafenib and doxorubicin; botezomib and sorafenib; erlotinib and fluorouracil; erlotinib, fluorouracil and interferon-$\alpha$; cisplatin and doxorubicin; and cisplatin, doxorubicin and erlotinib.

Preferred combinations for the treatment of metastasized colorectal cancers are: Irinotecan and Fluorouracil, irinotecan and erotinib, oxaliplatin and fluorouracil, FOLFOX (oxaliplatin, fluorouracil, lencovorin), cisplatin and doxocyclin.

Preferred combinations for the treatment of liver stage malaria are: Primaquine and clindamycin, primaquine and azithromycin, ciprofloxacin, doxocycline and atovaquone, primaquine, ciprofloxacin and rifampicin, primaquine, rifampicin and dapsone.

Preferred combinations for the treatment of chronic Hepatitis C are: Interferon-$\alpha$ and ribavirin, telepravir and ribavirin, telepravir, ribavirin and interferon-$\alpha$, Boceprevir and ribavirin, boceprevir, ribavirin and interferon-$\alpha$, Cyclosporin A and interferon-$\alpha$.

Preferred combinations for the treatment of Hepatitis B are: tenofovir and entecavir, tenofovir and interferon-$\alpha$, entecavir and interferon-$\alpha$, tenofovir, entecavir and interferon-$\alpha$.

Further information about drug, their actions and suitable combinations of drugs for the prevention and/or treatment of liver diseases or disorders can be taken from Chen, K. F., H. C. Yu, et al. (2010); Czauderna, P., G. Mackinlay, et al. (2002); Javle, M. and C. T. Hsueh (2009); Lee, J., J. O. Park, et al. (2004); Mendelsohn, J. and J. Baselga (2000); Patt, Y. Z., M. M. Hassan, et al. (2003); Richly, H., B. Schultheis, et al. (2009). Falcone; A., S. Ricci, et al. (2007); Javle, M. and C. T. Hsueh (2009); Sagar, J., K. Sales, et al. (2010); Seymour, M. T., T. S. Maughan, et al. (2007); Tournigand, C., T. Andre, et al. (2004); Kappe, S. H., A. M. Vaughan, et al. (2010); Goodman, C. D., V. Su, et al. (2007); Zeuzem, S. (2004). McHutchison, J. G., G. T. Everson, et al. (2009); Nelson, D R, Ghalib, R H, Sulkowski, M, et al. (2009). "EASL Clinical Practice Guidelines: management of chronic hepatitis B." J Hepatol 50(2): 227-242; Liaw, Y. F., N. Leung, et al. (2005); Lok, A. S. and B. J. McMahon (2009) Kornhuber, J., P. Tripal, et al. (2008); Gastaminza, P., C. Whitten-Bauer, et al. (2010).

Cell Penetrating Peptides

One or more cell penetrating peptide(s) (CCPs) can be coupled to the hydrophobic modified peptides of the invention in order to efficiently deliver prodrugs and intracellular active agents into hepatocytes. Preferably, CCPs will be used in combination with other compounds/drugs. Preferred embodiments are: N-terminally coupled CPPs and primaquine and or antibiotics for the treatment of malaria, N-terminally coupled CPPs and nucleoside analogues for the treatment of HBV and HCV, N-terminally coupled CPPs and protease inhibitors for the treatment of HCV and combinations thereof. In a preferred embodiment the CPP(s) are selected from polyarginine, Penetratin, HBVpreS2-TLM, Antennapedia.

N-terminally coupled CPPs can be used for the delivery of oligonucleotide-peptide conjugates and peptide nucleic acid conjugates into hepatocytes. One preferred embodiment is the delivery of sulfosuccinimidyl-4-(p-maleimidophenylbutyrate) coupled anti-HCV siRNA into hepatocytes using N-terminally coupled HIV-TAT peptides. Further details concerning CCPs can be taken from Meng, S., B. Wei, et al. (2009); de Koning, M. C., G. A. van der Marel, et al. (2003) and Zatsepin, T. S., J. J. Turner, et al. (2005).

Combination with a Label

In a further preferred embodiment, a drug is combined with a label that is one or more label(s) is coupled to the hydrophobic modified peptide of the present invention, to which one or more drug is coupled. Due to this combination the delivery of the drug to the liver can be monitored by detecting the label. The labels can be any kind of compound being suitable for diagnostic purposes and can be coupled to the hydrophobic modified peptide of the present invention by the methods described herein. Preferably the label is selected from a fluorescent dye, a radioisotope or a contrast agent. According to the present invention, a contrast agent is a dye or other substance that helps show abnormal areas inside the body. Preferred radioisotopes/fluorescence emitting isotopes are selected from the group consisting of alpha radiation emitting isotopes, gamma radiation emitting isotopes, Auger electron emitting isotopes, X-ray emitting isotopes, fluorescence emitting isotopes, such as $^{18}$F, $^{51}$Cr, $^{67}$Ga, $^{68}$Ga, $^{111}$In, $^{99m}$Tc, $^{140}$La, $^{175}$Yb, $^{153}$Sm, $^{166}$Ho, $^{88}$Y, $^{90}$Y, $^{149}$Pm, $^{177}$Lu, $^{47}$Sc, $^{142}$Pr, $^{159}$Gd, $^{212}$Bi, $^{72}$As, $^{72}$Se, $^{97}$Ru, $^{109}$Pd, $^{105}$Rh, $^{101m15}$Rh, $^{119}$Sb, $^{128}$Ba, $^{123}$I, $^{124}$I, $^{131}$I, $^{197}$Hg, $^{211}$At, $^{169}$Eu, $^{203}$Pb, $^{212}$Pb, $^{64}$Cu, $^{67}$Cu, $^{188}$Re, $^{186}$Re, $^{198}$Au and $^{199}$Ag. Preferred fluorescent dyes are selected from the following classes of dyes: Xanthens (e.g. Fluorescein), Acridines (e.g. Acridine Yellow), Oxazines (e.g. Oxazine 1), Cynines (e.g. Cy7/Cy 3), Styryl dyes (e.g. Dye-28), Coumarines (e.g. Alexa Fluor 350), Porphines (e.g. Chlorophyll B), Metal-Ligand-Complexes (e.g. PtOEPK), Fluorescent proteins (e.g APC, R-Phycoerythrin), Nanocrystals (e.g QuantumDot 705), Perylenes (e.g. Lumogen Red F300) and Phtalocyanines (e.g. IRDYE™700DX) as well as conjugates and combinations of these classes of dyes. Preferred contrast agents are selected from paramagnetic agents, e.g. Gd, Eu, W and Mn, preferably complexed with a chelating agent. Further options are supramagnetic iron (Fe) complexes and particles, compounds containing atoms of high atomic number, i.e. iodine for computer tomography (CT), microbubbles and carriers such as liposomes that contain these contrast agents.

Chelating Agent

The compound to be specifically delivered to hepatocytes may be bound to the hydrophobic modified peptide in the form of a complex with a chelating agent being able to form complexes with the respective compound. In a preferred embodiment of the invention, the chelating agent is selected from the group consisting of 1,4,7,10-tetraazacyclododecane-N,N',N,N'-tetraacetic acid (DOTA), ethylenediaminetetraacetic acid (EDTA), 1,4,7-triazacyclononane-1,4,7-triacetic acid (NOTA), triethylenetetramine (TETA), iminodiacetic acid, Diethylenetriamine-N,N,N',N',N"-pentaacetic acid (DTPA) and 6-Hydrazinopyridine-3-carboxylic acid (HYNIC), while 1,4,7,10-tetraazacyclododecane-N,N',N,N'-tetraacetic acid (DOTA) is particularly preferred.

Coupling of a Compound to the Hydrophobic Modified Peptide

The coupling of the compound(s) to the respective amino acids of X may be conducted by any suitable method known to the person skilled in the art.

In a preferred embodiment of the present invention, the compound(s) is/are coupled to the respective amino acid of X by using an activated ester. In particular, in case of coupling compounds(s) to the amino acids of X having an amino group in a side chain this method can be used. Alternatively, the following coupling methods can be used in order to couple one or more compound to the respective amino acids of X, which are shortly summarized. The specific reaction conditions for achieving a coupling of a compound to an amino acid with or without a linker can be easily determined by a chemist:

Formation of amides by the reaction of an amine and activated carboxylic acids, preferably NHS-esters or carbodiimides; a carbodiimide is a complete crosslinker that facilitates the direct conjugation of carboxyls to primary amine. NHS esters are reactive groups formed by carbodiimide-activation of molecules containing carboxylate groups Disulfide linkage using two thiols or one thiol that specifically reacts with pyridyl disulfides; Pyridyl disulfides react with sulfhydryl groups over a broad pH range (the optimum is pH 4-5) to form disulfide bonds. During the reaction, a disulfide exchange occurs between the molecule's SH-group and the 2-pyridyldithiol group. As a result, pyridine-2-thione is released.

Thioether formation using maleimides or haloacetyls and a thiol component; Haloacetyls react with sulfhydryl groups at physiologic pH. The reaction of the iodoacetyl group proceeds by nucleophilic substitution of iodine with a sulfur atom from a sulfhydryl group to result a stable thioether linkage. The maleimide group reacts specifically with sulfhydryl groups when the pH of the reaction mixture is between pH 6.5 and 7.5 and forms a stable thioether linkage that is not reversible.

Amidine formation using an imidoester and an amine; Imidoester crosslinkers react rapidly with amines at alkaline pH but have short half-lives. As the pH becomes more alkaline, the half life and reactivity with amines increases; therefore, crosslinking is more efficient when performed at pH 10 than at pH 8. Reaction conditions below pH 10 may result in side reactions, although amidine formation is favoured between pH 8-10

Hydrazide linkage using carbonyls (e.g. aldehydes) and hydrazides; Carbonyls (aldehydes and ketones) react with hydrazides and amines at pH 5-7. Carbonyls do not readily exist in proteins; however, mild oxidation of sugar glycols using sodium meta-periodate converts vicinal hydroxyls to aldehydes or ketones. Subsequent reaction with hydrazides results in the formation of a hydrazone bond.

Amine linkage using carbonyls and amines under reductive conditions; Reductive amination (also known as reductive alkylation) is a form of amination that involves the conversion of a carbonyl group to an amine via an intermediate imine. The carbonyl group is most commonly a ketone or an aldehyde.

Copper-catalyzed triazole formation using nitriles and azides. The Huisgen-type 1,3-dipolar cycloaddition between an azide and a terminal or internal alkyne is used to give stable 1,2,3-triazoles.

Isothiourea formation using isothiocyanates and amines; the reaction between isothiocyanates and amines, i.e. the ε-amino groups of lysine leads to a stable isothiourea bond.

Formation of esters by the reaction of an alcohol and activated carboxylic acids, preferably acid chlorides or carbodiimides; High temperature reaction allows direct reaction between alcohols and carboxylic acids to form stable esters, alternatively the carboxylic acids and be activated under acidic or base catalytic conditions.

Formation of ethers by the reaction of an alcohol and alkyl halides. Haloalkanes are reactive towards nucleophiles. They are polar molecules: the carbon to which the halogen is attached is slightly electropositive where the halogen is slightly electronegative. This results in an electron deficient (electrophilic) carbon which, inevitably, attracts nucleophiles.

Linker/Spacer for the Compound (e.g. a Drug)

The hydrophobic modified peptide, in particular the conjugates of the present invention, are preferably used to enrich a compound that is shuttled to the liver, in the liver. Preferably, the compound is cleaved off the conjugate with the hydrophobic modified peptide by a liver protein, preferably a hepatocellular proteolytic enzyme, in particular in vivo in the liver. The compound (e.g. drug) and the hydrophobic modified peptide form a conjugate. Preferably, the conjugate of compound and hydrophobic modified peptide is formed by covalent attachment or by complex formation. The form of attachment depends on the type of compound.

The coupling of the compound(s) (e.g. drug(s)) to the respective amino acids of X may be conducted by using a spacer or linker. Linker or spacer are known to the skilled artisan, such as polyalanine, polyglycin, carbohydrates, $(CH_2)n$ groups or amino acid sequences. The skilled artisan will, thus, be able to select the respective suitable linker(s) or spacer(s) depending on the respective application. The spacer or linker preferably comprises a recognition site for hepatocyte specific activation, which is preferably recognized by a liver or tumor specific protein. The recognition site is preferably a proteolytic cleavage site. The liver protein is, thus, preferably a hepatocellular protein, more preferably a hepatocellular proteolytic enzyme or a proteolytic enzyme which is overexpressed in a tumor, e.g. MMP7. Thus, the hydrophobic modified peptide can be administered to a subject and will be transported through the body, such as in the body fluids, without being cleaved. However, as soon as the hydrophobic modified peptide reaches its target, the liver or the hepatocytes, respectively, the liver protein, such as a hepatocellular proteolytic enzyme will cleave the proteolytic cleavage site and release the compound from its shuttle, i.e. the hydrophobic modified peptide.

Further preferred liver proteins are cytochromes, such as cytochrome P450 or lyases of the endocytic pathway. The HepDirect® technology (of Metabasis Technologies, Inc.) as used in Adefovir or Pradevofir, is also suitable for the present invention.

Of particular importance for tumor diseases like neoplastic alterations by metastases of carcinomas, e.g. colon carcinomas, is the interchange between malignant tissue and the surrounding tissue. There is a need for the activation of healthy epithelia cells and or the recruitment of immune cells which is a prerequisite for the formation of a distant metastasis of a primary tumor. Tissue analysis have shown that tumor specific mRNA expression levels of matrix-metallo-proteases (MMP1, MMP2, MMP7, MMP9 and MMP12) are associated with a bad prognosis of tumor patients (Gentner B. et al., Anticancer Res. 2009 January; 29(1):67-74). From these proteases especially MMP7 is of high interest since it is primarily expressed by tumor cells. Coupling a drug to the described peptide sequence via a linker sequence containing a specific proteolytic binding site for MMP7 (e.g a short Peptide Sequence GCHAK or RPLALWRS) but also all other MMP 7 substrates (e.g. Fibronectin, Elastin, Casein or others) would allow to deliver an inactive pro drug to the liver via the modification of the original peptide by means described above. In the liver the modified peptides would then be preferentially cleaved in the direct surrounding of the tumor tissue and the inactive pro drug would be activated. This method of drug delivery to the liver targeting primary hepatocellular carcinomas or metastasis in the liver overexpressing one of the above listed MMPs (e.g. Colon Carcinoma Metastasis) presents a novel way of targeting drugs to tumor tissues.

In one embodiment, the conjugate of compound and hydrophobic modified derived peptide is formed by complex formation. Preferred complexes useful in the invention are biotin/avidin, polyarginine/oligonucleotide (e.g. siRNA). The skilled artisan will be able to determine suitable complex components and to design the compound and hydrophobic modified peptide accordingly.

Prevention and/or Treatment of Liver Diseases

In a preferred embodiment of the invention the above hydrophobic modified peptides, in particular their conjugates with compounds, are provided for the prevention and/or treatment of a liver disease or disorder.

Depending on the liver disease or disorder which shall be prevented and/or treated the respective compound is selected and selectively, specifically delivered to the liver. A "liver disease" or a "liver disorder" according to the present invention refers to any disease or disorder that has an effect on or involves the organ liver, liver tissue or hepatocytes.

Examples of liver diseases are:
Hepatitis: inflammation of the liver, caused mainly by various viruses but also by certain poisons, autoimmunity or hereditary conditions;
Cirrhosis: the formation of fibrous tissue in the liver, replacing dead liver cells. The death of the liver cells can for example be caused by viral hepatitis, alcoholism or contact with other liver-toxic chemicals;
Haemochromatosis: a hereditary disease causing the accumulation of iron in the body, eventually leading to liver damage;
Cancer of the liver: primary hepatocellular carcinoma (HCC) or cholangiocarcinoma and metastatic cancers, usually from other parts of the gastrointestinal tract;
Wilson's disease: a hereditary disease which causes the body to retain copper;
Primary sclerosing cholangitis: an inflammatory disease of the bile duct, autoimmune in nature;
Primary biliary cirrhosis: autoimmune disease of small bile ducts;
Budd-Chiari syndrome: obstruction of the hepatic vein;
Gilbert's syndrome: a genetic disorder of bilirubin metabolism, found in about 5% of the population;
Glycogen storage disease type II: the build-up of glycogen causes progressive muscle weakness (myopathy) throughout the body and affects various body tissues, particularly in the heart, skeletal muscles, liver and nervous system;
pediatric liver disease, such as biliary atresia, alpha-1-antitrypsin deficiency, alagille syndrome, and progressive familial intrahepatic cholestasis;
metabolic diseases.

Furthermore, also liver diseases of animals, such as pets or livestock, are included, in particular diseases that can be transmitted to humans, such as toxoplasmosis.

The liver disease or disorder to be prevented and/or treated is preferably selected from hepatitis, cirrhosis, haemochromatosis, preferably hepatitis caused by hepatitis A, B, C, D, E, F, G and H virus. The liver disease or disorder to be prevented and/or treated can also be concomitant hepatitis caused by viruses, such as viruses of the family Herpesviridae, e.g. herpes virus, cytomegalic virus (CMV) but also varicella zoster virus (VZV), Epstein Barr virus (EBV), coxsackie viruses, yellow fever virus, Dengue virus.

The liver disease or disorder to be prevented and/or treated can also be a disease which involves a liver stadium of a virus or a non-viral pathogen, such as in many tropical diseases. Since the liver stadium of some pathogens is an early stadium, the respective infection can be selectively, specifically treated in such an early stadium. Such viruses are hepatitis A, B, C, D, E, F, G and H virus, herpes viruses.

Such non-viral pathogens are bacteria, parasites and/or worms. Parasites are for example protozoan parasites of the genus *Plasmodium* that cause malaria, such as *Plasmodium falciparum, Plasmodium vivax*, and related species (e.g. *Plasmodium ovale, Plasmodium malariae, Plasmodium knowles*[iota]). Such worms are for example flatworms of the genus *Schistosoma* that cause schistosomiasis or bilharziosis, such as *Schistosoma mansoni, Schistosoma intercalatum, Schistosoma haematobium, Schistosoma japonicum* and *Schistosoma mekongi*. Such parasites are also for example *Leishmania* trypanosome protozoa of the genus *Phlebotomus* and *Lutzomyia* which are responsible for the disease leishmaniasis. Therefore, malaria, schistosomiasis (bilharziosis), and/or leishmaniasis can be prevented and/or treated by the means of this invention. Therefore, certain tropical diseases can be prevented and/or treated by the means of this invention.

The liver diseases or disorders to be prevented and/or treated are preferably liver tumors, preferably hepatocellular carcinoma (HCC) or neoplastic alterations by metastases of solid tumors, e.g. colon carcinomas. The liver disease or disorder to be prevented and/or treated can also be a metabolic disease, such as diabetes, hyperlipidemia, metabolic syndrome and obesity, chronic hyperglycemia, metabolic syndrome, non-alcoholic steatohepatitis (NASH) (see also (9)).

In a preferred embodiment of the invention the above hydrophobic modified peptides, in particular their conjugates with compounds, are provided for the regulation of liver function(s).

Preferred is their use for hepatocyte-mediated antigen presentation and activation of liver-directed immunological responses. In this case, the compound to be delivered to the liver is preferably an immunogenic epitope.

In a preferred embodiment of the invention the above described hydrophobic modified, preferably acylated derived peptides, in particular their conjugates with compounds, can be used for the manufacture of a medicament for the prevention and/or treatment of a liver disease or disorder.

Pharmaceutical Compositions

As outlined above, the present invention provides a pharmaceutical composition comprising at least one hydrophobic modified peptide as defined herein and at least a compound to be specifically delivered to the liver as defined herein and optionally a pharmaceutically acceptable carrier and/or excipient.

The pharmaceutical composition according to the present invention comprises:
  at least one hydrophobic modified peptide as defined herein above; and
  optionally a pharmaceutically acceptable carrier and/or excipient.

The pharmaceutical compositions according to the present invention are very well suited for all the uses and methods described herein.

A "pharmaceutically acceptable carrier or excipient" refers to any vehicle wherein or with which the pharmaceutical or vaccine compositions according to the invention may be formulated. It includes a saline solution, such as phosphate buffer saline, a citrate buffer, NaCl, ocytl glucoside and/or a poloxamere. In general, a diluent or carrier is selected on the basis of the mode and route of administration, and standard pharmaceutical practice.

Treatment Method

Furthermore, and as outlined above, the present invention provides methods for prevention and/or treatment of a liver disease or disorder by utilizing the above described hydrophobic modified peptide(s) or the pharmaceutical composition(s) of the invention.

The present invention also provides a method for the prevention and/or treatment of a liver disease or disorder by administering to a subject a conjugate as defined herein, which comprises a hydrophobic modified derived peptide and a compound (e.g. a drug), or a pharmaceutical composition as defined herein. The method for the prevention and/or treatment of a liver disease or disorder according to the present invention comprises administering to a subject in a therapeutically effective amount
(a) a hydrophobic modified peptide as defined herein above and comprising at least a compound (e.g. a drug) as defined herein above, or
(b) a pharmaceutical composition as defined herein above.

Route of Administration

Preferably, the route of administration of the conjugates or pharmaceutical compositions of the present invention, in particular in the method of treatment, is selected from subcutaneous, intravenous, oral, nasal, intramuscular, transdermal, inhalative, by suppository. A preferred embodiment for nasal administration or application is a nasal spray.

In a further preferred embodiment, the hydrophobic modified peptide of the invention comprising a compound (e.g. a drug) is dissolved in serum from the patient and is applied via injection.

Therapeutically Effective Amount

A "therapeutically effective amount" of a hydrophobic modified peptide or a pharmaceutical composition of this invention refers to the amount that is sufficient to prevent and/or treat the respective liver disease or disorder. The preferred therapeutically effective amount depends on the respective compound that is to be delivered and its respective therapeutic potential. The skilled artisan will be able to determine suitable therapeutically effective amounts. In a preferred embodiment, the therapeutically effective amount is in the range of 10 pmol per kg to 20 μmol per kg body weight. For use as a therapeutic agent (i.e. a drug is coupled to the hydrophobic modified peptide) a preferred amount to be applied to a patient is in the range of 100 nmol per kg to 2 μmol per kg body weight.

Preferred Hydrophobic Modified Peptides of the Invention

In the following, preferred hydrophobic modified peptides of the invention are given. These hydrophobic modified peptides are based on the amino acid sequence KKKNLSTSNPLGFFPDHQLPD (SEQ ID NO. 14) or KKKNLSTSNPLGFFPDHQLDP (SEQ ID NO. 15), wherein one or two of the N-terminal lysines (K) may be deleted or substituted by another amino acid.

An exemplary hydrophobic modified peptide has the following chemical structure:

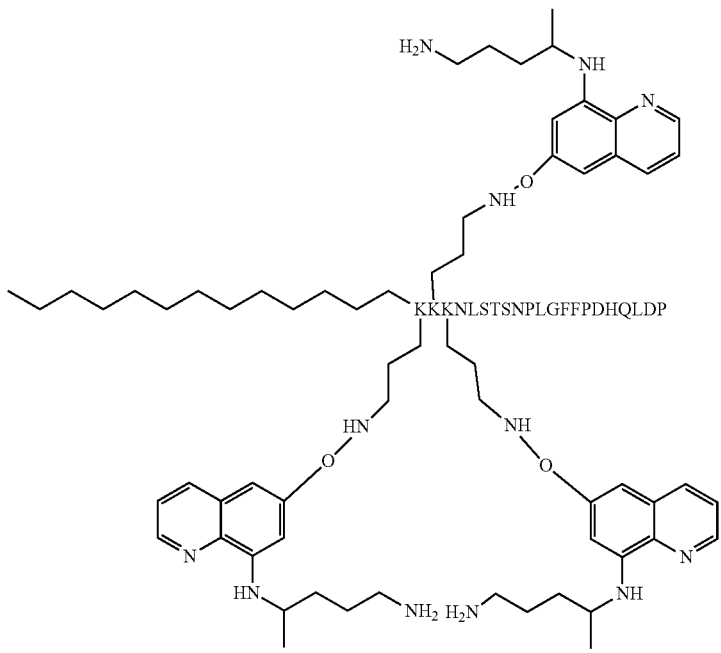

The amino acid sequence of the compound having the above exemplified chemical structure is stearoyl-[K(primaquine)][K(primaquine)][Kprimaquine)]-NLSTSNPLGFFPDHQLDP (SEQ ID NO:15), wherein to each of the three N-terminal lysines (KKK) a primaquine molecule is coupled, and the first N-terminal lysine is further modified with a hydrophobic stearoyl group. In this connection it should be noted that the formulas of the hydrophobic modified peptides of the invention are simplified in the text so that the above exemplified hydrophobic modified peptide can be also designated "stearoyl-[K(primaquine)]$_3$-NLSTSNPLGFFPDHQLDP (SEQ ID NO:15)"

A further exemplary preferred hydrophobic modified peptide has the following chemical structure:

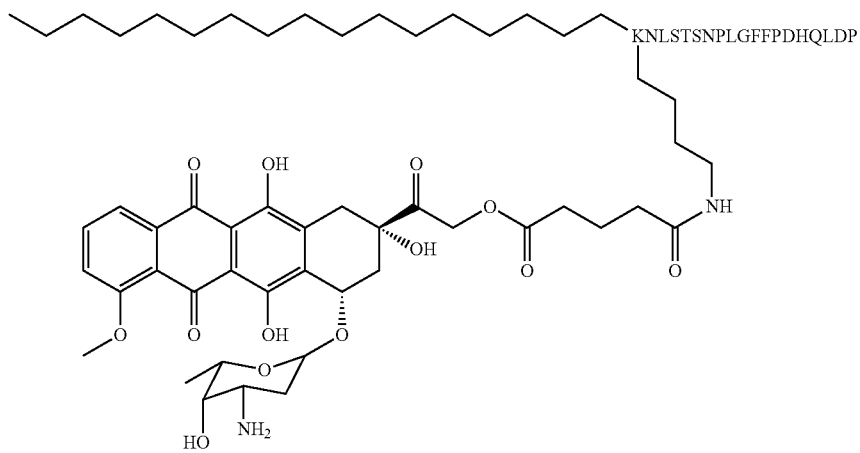

Myristoyl-[K-Doxorubicin]-NLSTSNPLGFFPDHQLDP (SEQ ID NO:21) (HBVpreS/myr-[K-Doxorubicin]3-20)

A further preferred exemplary hydrophobic modified peptide has the following chemical structure:

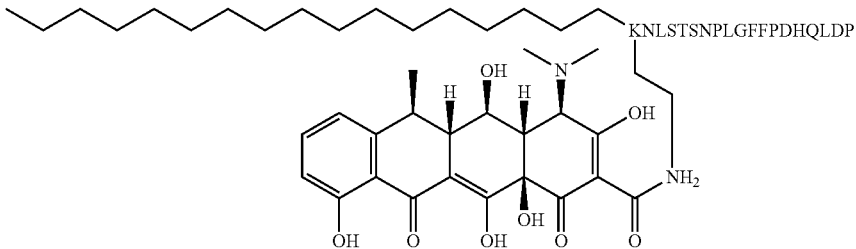

Myristoyl-[K-Levofloxacin]-NLSTSNPLGFFPDHQLDP (SEQ ID NO:21) (HBVpreS/myr-[K-Levofloxacin]3-20)

In the following, preferred hydrophobic modified peptides of the invention as well as their preferred specific uses in treatment and/or prevention of diseases or disorders of the liver are given:

Stearoyl-[K(primaquine)]$_3$-NLSTSNPLGFFPDHQLDP (SEQ ID NO:15) (and stearoyl-[K(GCHAK-primaquine)]-NLSTSNPLGFFPDHQLDP (SEQ ID NO:21 preferably for use in the treatment of the liver stage of malaria, especially Malaria tertian;

Myristoyl-[K(Doxocyclin)]$_3$-NLSTSNPLGFFPD-HQLDP (SEQ ID NO:15) and myristoyl-[K(GCHAK Doxocylin)]$_3$-NLSTSNPLGFFPDHQLDP (SEQ ID NO:15)-preferably for use in the treatment of MMP 7 overexpressing neoplastic alterations in the liver;

Myristoyl-[K(Penicillin)]$_3$-NLSTSNPLGFFPDHQLDP (SEQ ID NO:15) and myristoyl-[K(GCHAK(SEQ ID NO:19) Penicillin)]$_3$-NLSTSNPLGFFPDHQLDP (SEQ ID NO:15) preferably for use in the treatment of bacterial infections in the liver;

Myristoyl-[K(Cyclosporine)]$_3$-NLSTSNPLGFFPD-HQLDP (SEQ ID NO:15) and myristoyl-[K(GCHAK (SEQ ID NO:19) Cyclosporine))]$_3$-NLSTSNPLGFFP-DHQLDP (SEQ ID NO:15) preferably for use in treatment of patients preceding and following liver transplantation;

Myristoyl-[K(Rapamune™)]$_3$-NLSTSNPLGFFPD-HQLDP (SEQ ID NO:15) and myristoyl-[K(GCHAK (SEQ ID NO:19) Rapamune™)]$_3$-NLSTSNPLGFFP-DHQLDP (SEQ ID NO:15) preferably for use in treatment of patients preceding and following liver transplantation;

Stearoyl-[K(RPLALWRS (SEQ ID NO:20)-Velcade™)]$_3$-NLSTSNPLGFFPDHQLDP (SEQ ID NO:15) preferably for use in the inhibition of neoangiogenesis in neoplastic alterations of the liver;

Stearoyl-[K(Nexavar™)]$_3$-NLSTSNPLGFFPDHQLDP (SEQ ID NO:15) and Stearyl-[K(RPLALWRS (SEQ ID NO:20)-Nexavar™)]$_3$-NLSTSNPLGFFPDHQLDP (SEQ ID NO:15) preferably for use in the inhibition of neoangiogenesis in neoplastic alterations of the 1 liver; and Stearoyl-[K(Thiazolidinedione)]$_3$-NLSTSNPLGFFPD-HQLDP (SEQ ID NO:15) preferably for use in the treatment of steatosis, diabetis mellitus type 2 and the inhibition of neoangenesis.

Stearoyl-[K(primaquine)]$_3$-NLSTSNPLGFFPDHQLPD (SEQ ID NO:14) and stearoyl-[K(GCHAK-primaquine) (SEQ ID NO:19)]-NLSTSNPLGFFPDHQLPD (SEQ ID NO:14) preferably for use in the treatment of the liver stage of malaria, especially Malaria tertian;

Myristoyl-[K(Doxocyclin)]$_3$-NLSTSNPLGFFPD-HQLPD (SEQ ID NO:14) and myristoyl-[K(GCHAK (SEQ ID NO:19) Doxocylin)]$_3$-NLSTSNPLGFFPD-HQLPD (SEQ ID NO:14) preferably for use in the treatment of MMP 7 overexpressing neoplastic alterations in the liver;

Myristoyl-[K(Penicillin)]$_3$-NLSTSNPLGFFPDHQLPD (SEQ ID NO:14) and myristoyl-[K(GCHAK (SEQ ID NO:19) Penicillin)]$_3$-NLSTSNPLGFFPDHQLPD (SEQ ID NO:14) preferably for use in the treatment of bacterial infections in the liver;

Myristoyl-[K(Cyclosporine)]$_3$-NLSTSNPLGFFPD-HQLPD (SEQ ID NO:14) and myristoyl-[K(GCHAK (SEQ ID NO:19) Cyclosporine)]$_3$-NLSTSNPLGFFP-DHQLPD (SEQ ID NO:14) preferably for use in treatment of patients preceding and following liver transplantation;

Myristoyl-[K(Rapamune™)]$_3$-NLSTSNPLGFFPD-HQLPD (SEQ ID NO:14) and myristoyl-[K(GCHAK (SEQ ID NO:19) Rapamune™)]$_3$-NLSTSNPLGFFP-DHQLPD (SEQ ID NO:14) preferably for use in treatment of patients preceding and following liver transplantation;

Stearoyl-[K(RPLALWRS (SEQ ID NO:20)-Velcade™)]$_3$-NLSTSNPLGFFPDHQLPD (SEQ ID NO:14) preferably for use in the inhibition of neoangiogenesis in neoplastic alterations of the liver;

Stearoyl-[K(Nexavar™)]$_3$-NLSTSNPLGFFPDHQLPD (SEQ ID NO:14) and Stearyl-[K(RPLALWRS (SEQ ID NO:20)-Nexavar™)]$_3$-NLSTSNPLGFFPDHQLPD (SEQ ID NO:14) preferably for use in the inhibition of neoangiogenesis in neoplastic alterations of the liver;

Stearoyl-[K(Thiazolidinedione)]$_3$-NLSTSNPLGFFPD-HQLPD (SEQ ID NO:14) preferably for use in the treatment of steatosis, diabetis mellitus type 2 and the inhibition of neoangenesis;

Myristoyl-[K-Doxorubicin]-NLSTSNPLGFFPDHQLDP (SEQ ID NO:21) preferably for use in the treatment of cancer, preferably primary HCC (hepatocellular carcinoma) or malaria; and Myristoyl[K-Levofloxacin]-NLSTSNPLGFFPDHQLDP (SEQ ID NO:21) (HBVpreS/myr-[K-Levofloxacin]3-20y) for the treatment of malaria.

TABLE 1

Preferred hydrophobic modified peptides

| Hydrophobic modified Peptide | Coupled Agent | Application |
|---|---|---|
| stearoyl-[K(Primaquine)]₃-NLSTSNPLGFFPDHQLDP (SEQ ID NO: 15) | Primaquine | Treatment of Malaria Tertia |
| myristoyl-[K(Doxocyclin)]₃-NLSTSNPLGFFPDHQLDP (SEQ ID NO: 15) | Doxocyclin | Treatment of MMP7 overexpressing neoplastic alterations in the liver |
| myristoyl-[K(Penicillin)]₃-NLSTSNPLGFFPDHQLDP (SEQ ID NO: 15) | Penicillin | Treatment of bacterial infections in the liver |
| stearoyl-[K(RPLALWRS-Velcade ™)]₃-NLSTSNPLGFFPDHQLDP (SEQ ID NO: 15) | Velcade ™ | Inhibition of neoangiogenesis |
| myristoyl-[K(Rapamune ™)]₃-NLSTSNPLGFFPDHQLDP (SEQ ID NO: 15) | Rapamune ™ | For the treatment of patients preceding and following liver transplantation |
| myristoyl-[K(Cyclosporine)]₃-NLSTSNPLGFFPDHQLDP (SEQ ID NO: 15) | Cyclosporine ™ | For the treatment of patients preceding and following liver transplantation |
| stearoyl-[K(Thiazolidinedione)]₃-NLSTSNPLGFFPDHQLDP (SEQ ID NO: 15) | Thiazolidinedione (glitazones) | Treatment of Diabetis Mellitus Type 2, Steatosis and neoangiogenesis in the liver |
| stearoyl-[K(Nexavar ™)]₃-NLSTSNPLGFFPDHQLDP (SEQ ID NO: 15) | Nexavar ™ | Inhibition of neoangiogenesis in the liver |
| Myristoyl-[K-Doxorubicin]-NLSTSNPLGFFPDHQLDP | Doxorubicin | First line drug for primary HCC; anti-malaria drug |
| Myristoyl-[K-Levofloxacin]-NLSTSNPLGFFPDHQLDP (SEQ ID NO: 15) | Levofloxacin | Treatment of Malaria Tertia by inhibition of the liver stage of malaria |
| stearoyl-[K(Primaquine)]₃-NLSTSNPLGFFPDHQLPD (SEQ ID NO: 14) | Primaquine | Treatment of Malaria Tertia |
| myristoyl-[K(Doxocyclin)]₃-NLSTSNPLGFFPDHQLPD (SEQ ID NO: 14) | Doxocyclin | Treatment of MMP7 overexpressing neoplastic alterations in the liver |
| myristoyl-[K(Penicillin)]₃-NLSTSNPLGFFPDHQLPD (SEQ ID NO: 14) | Penicillin | Treatment of bacterial infections in the liver |
| stearoyl-[K(RPLALWRS-Velcade ™)]₃-NLSTSNPLGFFPDHQLPD (SEQ ID NO: 14) | Velcade ™ | Inhibition of neo angiogenesis |
| myristoyl-[K(Rapamune ™)]₃-NLSTSNPLGFFPDHQLPD (SEQ ID NO: 14) | Rapamune ™ | For the treatment of patients preceding and following liver transplantation |
| myristoyl-[K(Cyclosporine)]₃-NLSTSNPLGFFPDHQLPD (SEQ ID NO: 14) | Cyclosporine ™ | For the treatment of patients preceding and following liver transplantation |
| stearoyl-[K(Thiazolidinedione)]₃-NLSTSNPLGFFPDHQLPD (SEQ ID NO: 14) | Thiazolidinedione (glitazones) | Treatment of Di ab eti s Mellitus Type 2, Steatosis and neoangiogenesis in the liver |

TABLE 1-continued

Preferred hydrophobic modified peptides

| Hydrophobic modified Peptide | Coupled Agent | Application |
|---|---|---|
| stearoyl-[K(Nexavar ™)]₃-NLSTSNPLGFFPDHQLPD (SEQ ID NO: 14) | Nexavar ™ | Inhibition of neoangiogenesis in the liver | myr refers to myristoylation of the N-terminus; palm refers to palmitoylation of the N-terminus; stearoyl refers to stearoylation of the N-terminus;

The following examples and drawings illustrate the present invention without, however, limiting the same thereto.

BRIEF DESCRIPTION OF THE FIGURES

FIG. 4A Specific enrichment of 400 nmol/kg stearoyl-[K(DOTA[$^{68}$Ga])]₃-NLSTSNPLGFFPDHQLDP (SEQ ID NO:15)-amide in the liver of a WAG/Rji rat five minutes post i.v. injection. FIG. 4B Counterstain using $^{18}$F-FDG 24 hours after the initial measurement $^{18}$F-FDG is enriched in organs consuming high amounts of glucose, in the picture the heart (grey mass on the top) and the tumour enrich glucose ($^{18}$F-FDG enriched in the brain is not shown for technical reasons). FIG. 4C Merge of both images demonstrating the specificity of the peptides staining only liver tissue but not the tumor tissue.

FIG. 6: Cell Viability Assay with Primary Mouse Hepatocytes. FIG. 6A 12 h measurement of primary mouse hepatocytes incubated for 12 h with doxorubicin coupled to N-terminally modified preS peptides (Conjugate) and controls. FIG. 6B 24 h measurement of primary mouse hepatocytes incubated for 12 h with doxorubicin coupled to N-terminally modified preS peptides (Conjugate) and controls.

FIG. 8: PET summary images of rats injected with Myristoyl-[K-Levofloxacin]-NLSTSNPLGFFPDHQLDPy (SEQ ID NO:21)-$^{131}$I (HBVpreS/myr-[K-Levofloxacin]3-20y-$^{131}$I).

EXAMPLES

Figure 1:
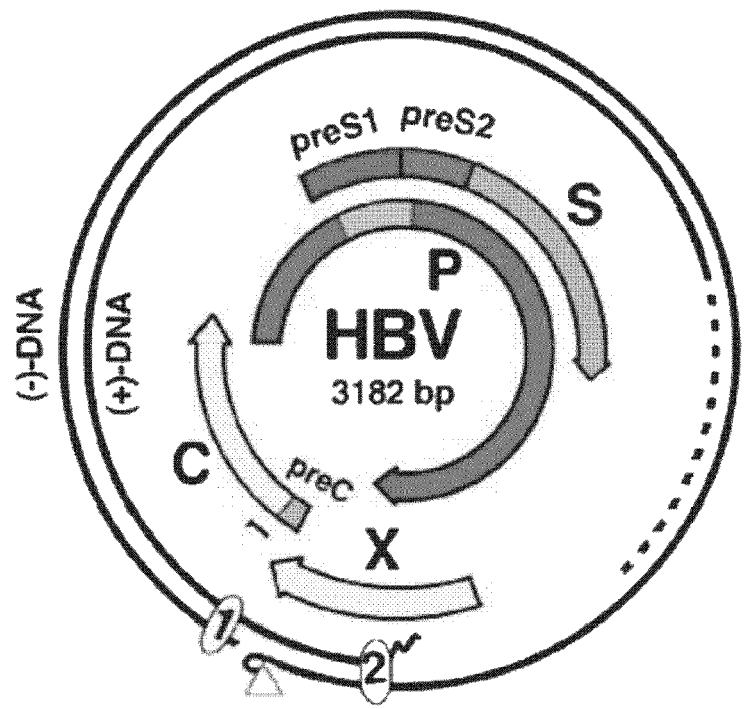
FIG. 1: Schematic representation of the HBV particle and the HBV L-, M- and S-proteins. The partially double stranded DNA is covalently associated with the viral polymerase complex, consisting of the terminal protein, (TP), the reverse transcriptase (RT) and the RNaseH. The genome is encapsulated by an icosahedral shell, built of 120 core-protein dimers. The 3 HBV surface proteins L-, M- and S- are embedded into an ER-derived lipid bilayer. The L- and M-proteins contain the complete S-domain serving as a membrane anchor. Schematic representation of the partially double stranded DNA genome of HBV; C=Core protein forming the viral capsid; X=X Protein, a pleiotropic trans-activator with undefined function; P=Viral Polymerase; preS1/preS2/S combinations of these form the large (preS1/preS2/S) HBV surface protein (L Protein) the medium (preS2/S) HBV surface protein and the small (S) HBV surface protein.
Figure 1:
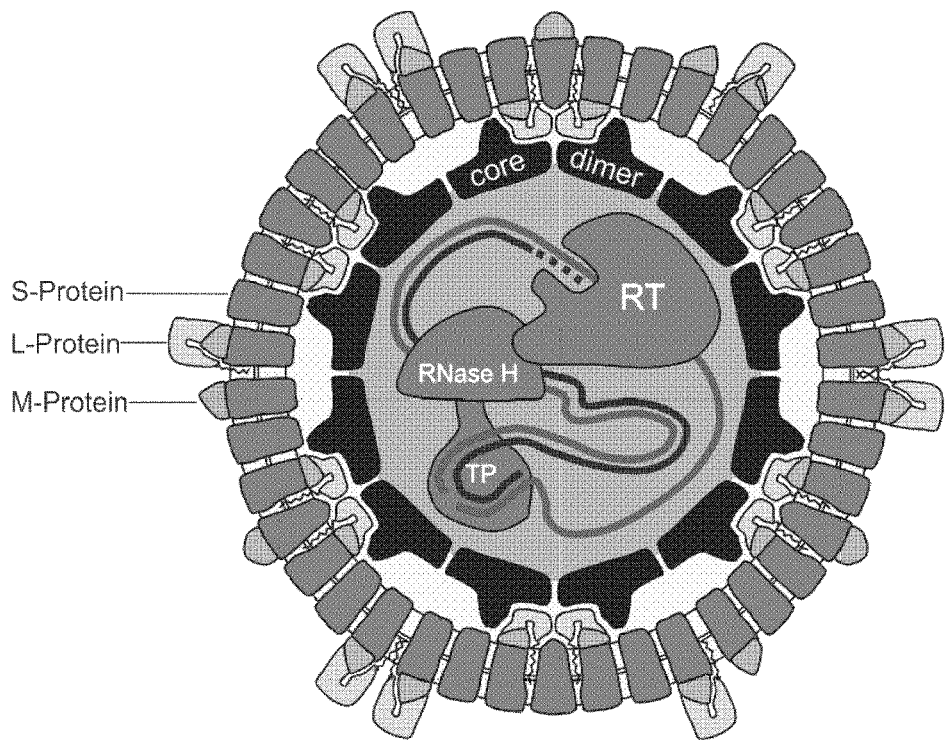
Figure 2:
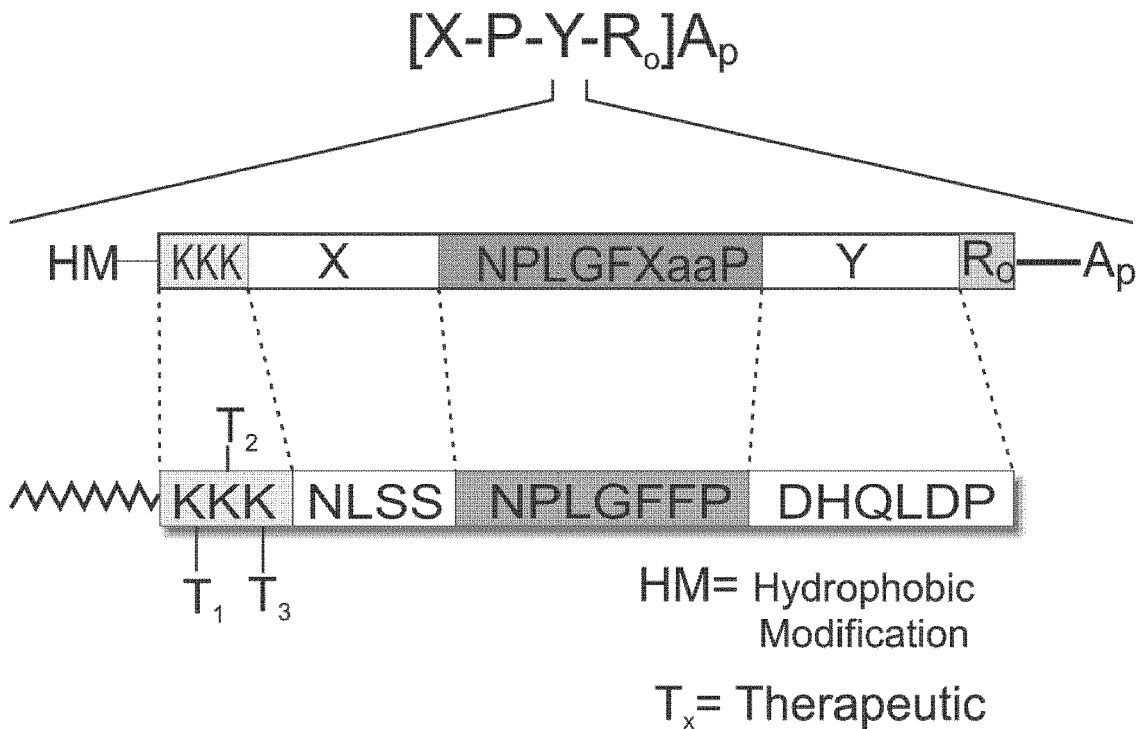
FIG. 2: Schematic diagram of the general formula of the hydrophobic modified peptide of the present invention and an example of a hydrophobic modified peptide of the invention.
Figure 3:
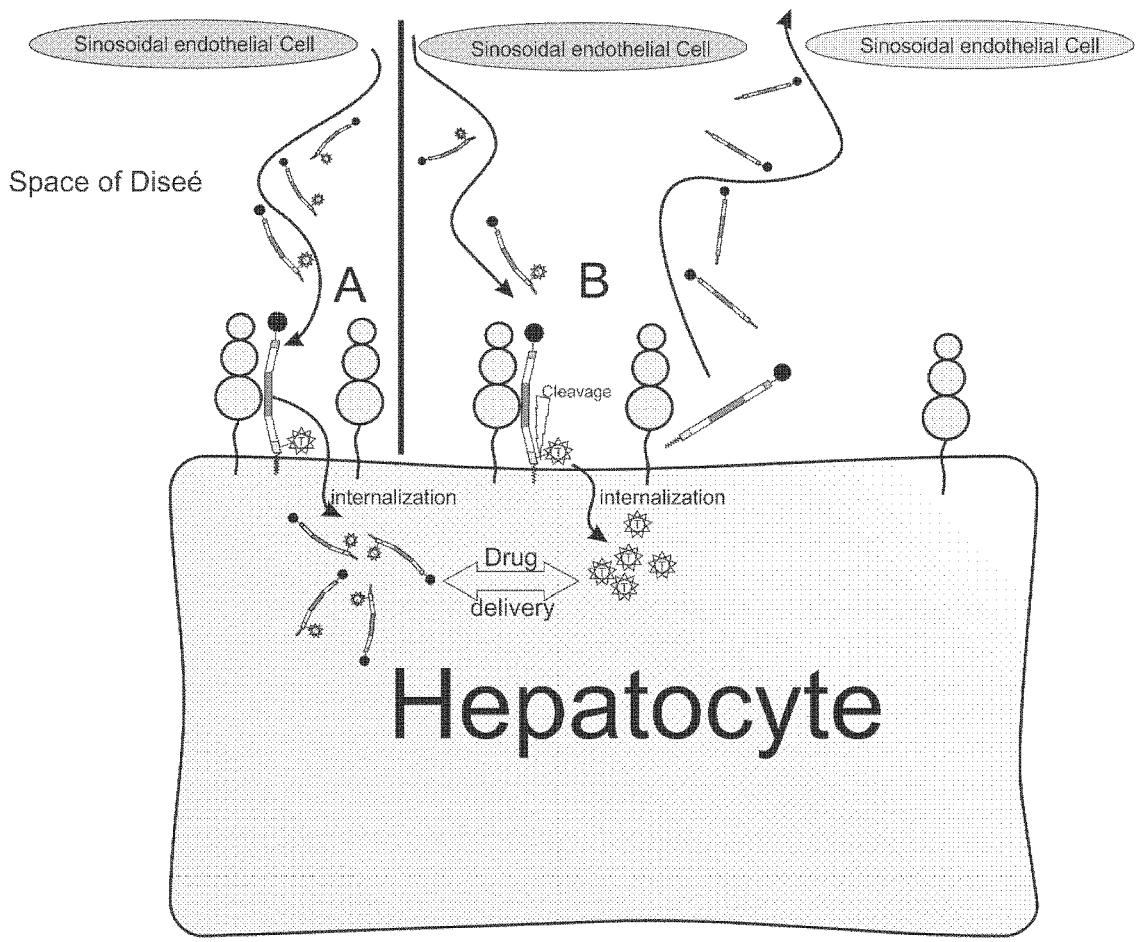
FIG. 3: Schematic diagram of the binding of a hydrophobic modified peptide of the invention to the surface of a hepatocyte.

In the following examples 1 and 2, a hydrophobic peptides carrying Gd as a label complexed with DOTA (stearoyl-[K(DOTA[Gd])]₃-NLSTSNPLGFFPDHQLDP (SEQ D NO:15)-amide was used in order to demonstrate the working principle of the present invention.

Example 1

Synthesis of the Hydrophobic Modified Peptide

The synthesis of the peptides was carried out by using the Fmoc method as described in (10) Gripon, P. et al. J Virol 79, 1613-1622 (2005).

Synthesis DOTA-DFP

Diisopropylcarbodiimide (5 mmol, 631 mg, 774 µl) was dissolved in pyridine (15 ml) and dropped over 10 min to a solution of DOTA (5 mmol, 2.02 g) and difluoro phenole (5 mmol, 650 mg) in water (60 ml) while stirring. 30 min after addition, the reaction mixture was extracted three times with dichlormethane and the aqueous phase was evaporated to dryness by using a rotating evaporator. The crude product was dissolved in a mixture of water (11 ml) and acetonitrile (3 ml) and was purified via preparative RP-HPLC. The HPLC fractions containing the product were concentrated by lyophilisation. Yield: 1.0633 g (41%).

Coupling to the Peptide

The peptide stearoyl-KKKNLSTSNPLGFFPDHQLDP (SEQ NO:15)-amide (140 mg, 0.055 mmol) was dissolved in 5 ml DMF. DOTA-DFP (129 mg, 0.25 mmol) was added and, furthermore, DIPEA (410 µl, 2.5 mmol) was added. The mixture was stirred over night at 50° C. Diethylether was added until precipitation; the precipitate was separated by using a centrifuge and was washed twice with diethylether. The crude product was purified by using RP-HPLC. The purification was effected by using a gradient of water and acetonitrile, both comprising 0.1% trifluoroacetic acid. The HPLC fractions containing the product were concentrated by lyophilisation. Yield: 112 mg (55%).

Complexing of $Gd^{3+}$

The peptide stearoyl-[K(DOTA)]$_3$-NLSTSNPLGFFPD-HQLDP (SEQ ID NO:15)-amide (112 mg, 0.030 mmol) was dissolved in 0.4 M sodium acetate buffer (pH 5) and $GdCl_3*6\ H_2O$ (335 mg, 0.90 mmol) was added. The mixture was heated for 1 h in a water bath while stirring. The resulting mixture of products was purified by using RP-HPLC. The purification was effected by using a gradient of water and acetonitrile, both comprising 0.1% trifluoroacetic acid. The HPLC fractions containing the product (stearoyl-[K(DOTA[Gd])]$_3$-NLSTSNPLGFFPDHQLDP (SEQ ID NO:15)-amide) were concentrated by lyophilisation. Yield: 94 mg (77%).

Example 2

Imaging in PET

Figure 4:
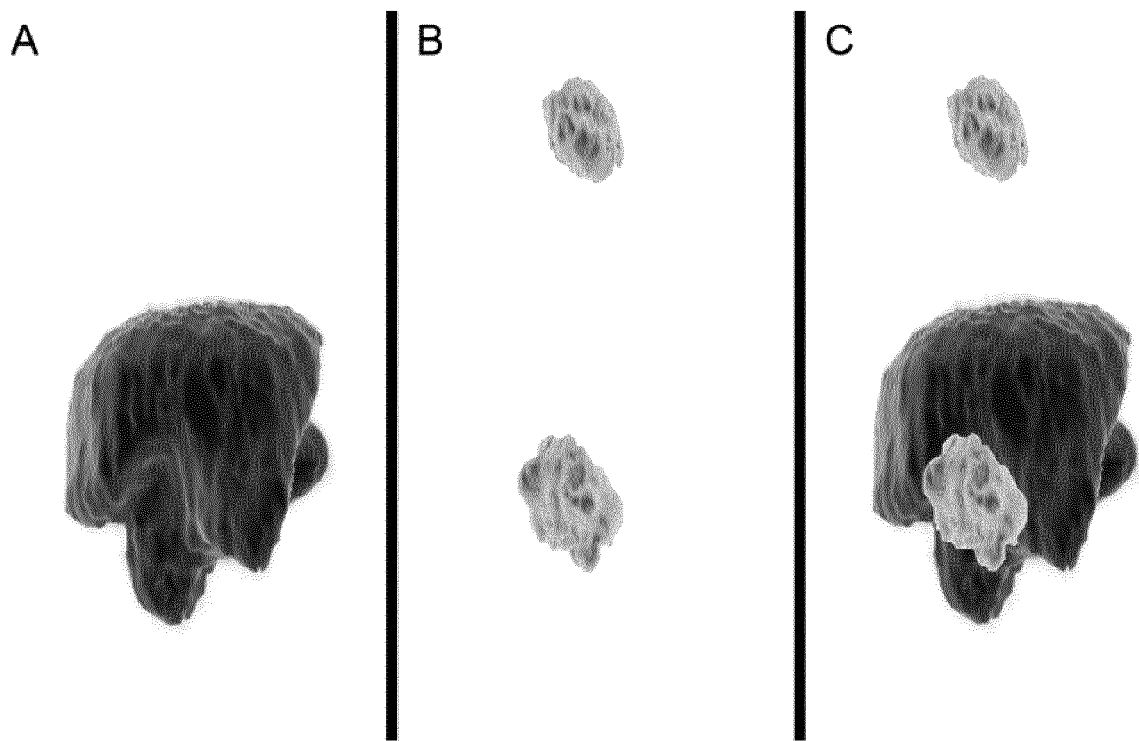
FIG. 4: PET image of a tumor bearing rat.

The peptide stearoyl-[K(DOTA[$^{68}$Ga])]$_3$-NLSTSNPL-GFFPDHQLDP (SEQ ID NO:15)-amide was dissolved in citrate buffer (pH 8.0)+4% BSA and injected i.v. in the tail vene of tumour bearing WAG/Rij rats. The rats were orthopically injected with 1×10$^6$ syngenic colon carcinoma cells (CC531 cells) 10 days prior to the measurements. At the day of measurement the rats received the peptide in a concentration of 400 nmol/kg body weight. During the experiments the rats were anaesthetised by isoflurane and kept at 37° C. PET imaging was performed using a Inveon small animal PET from Siemens, imaging was started immediately after i.v. injection of the peptide 24 h after the initial measurement using stearoyl-[K(DOTA[$^{68}$Ga])]$_3$-NLSTSNPLGFFPD-HQLDP-amide the rats were injected with $^{18}$F-FDG (Fluodeoxyglucose($^{18}$F)) in a concentration of 5 millicuries as a control. FIG. 4A-C shows a representative PET image of a tumor bearing rat. FIG. 4A Specific enrichment of 400 nmol/kg stearoyl-[K(DOTA[$^{68}$Ga])]$_3$-NLSTSNPLGFFPD-HQLDP (SEQ ID NO:15)-amide in the liver of a WAG/Rji rat five minutes post i.v. injection. FIG. 4B Counterstain using $^{18}$F-FDG 24 hours after the initial measurement $^{18}$F-FDG is enriched in organs consuming high amounts of glucose, in the picture the heart (grey mass on the top) and the tumour enrich glucose ($^{18}$F-FDG enriched in the brain is not shown for technical reasons). FIG. 4C Merge of both images demonstrating the specificity of the peptides staining only liver tissue but not the tumor tissue.

Example 3

Test of Liver Specificity and Cytotoxicity of N-Terminally Modified preS Peptides Coupled with Doxorubicin Doxorubicin coupled peptides have been synthesized as described herein. Briefly, FMOC protected solid phase peptide synthesis was used to synthesize the peptide backbone (KNLSTSNPLGFFPDHQLDPy (SEQ ID NO:21)), Doxorubicin was then coupled to the peptide backbone using amid formation. The "y" in the peptide backbone represents D-tyrosine to which $^{131}$Iodine can be coupled to act as a label for detecting the modified peptide in rats. The resulting peptide was purified by HPLC and purity was analyzed by Mass Spectrometry. Purity of the resulting peptide was 97% or higher.

A sketch of the modified peptide is shown below:

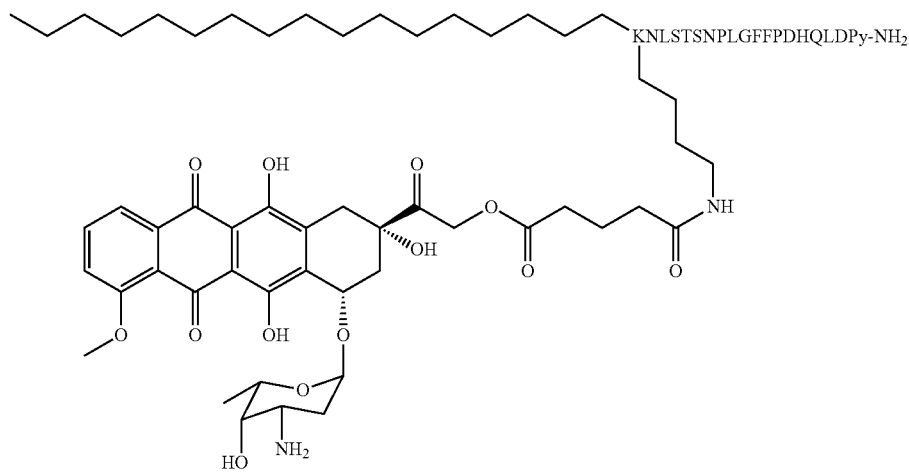

Myristoyl-[K-Doxorubicin]-NLSTSNPLGFFPDHQLDPy (SEQ ID NO:21)-amide (HBVpreS/myr-[K-Doxorubicin]3-20y)

In order to show that the resulting synthesized peptides was still liver specific, the above sketched peptide was labeled C-terminally with radioactive $^{131}$Iodine using the chloramine T method as described in (Eisenhut and Mier, 2011; 36).

Tyrosine Specific Iodine Labeling:

100 of a 1 mM peptide solution (solved in water) is added to 20 µl phosphate buffer. Varying amounts of radioactive Na$^{131}$I solution is added to the peptide solution as required to achieve complete labeling, the amount varies based on the age of the radioactive Na$^{131}$I solution. The skilled artisan can control the required amounts by measuring radioactive activity (counts). 5 µl chloramine-T solution (2 mg/ml in water) is then added and the resulting solution is vortexed (5 times) and centrifuged (8000 g, 30 s, 5 times). Thereafter 10 µl of a saturated methionine solution is added and the vial is carefully inverted to mix. The resulting solution is then purified using RP-HPLC. The peptide fraction is collected and vacuum dried. The lyophilized, marked peptide can then be resolved in the desired experimental buffer and used for downstream experiments.

Figure 5:
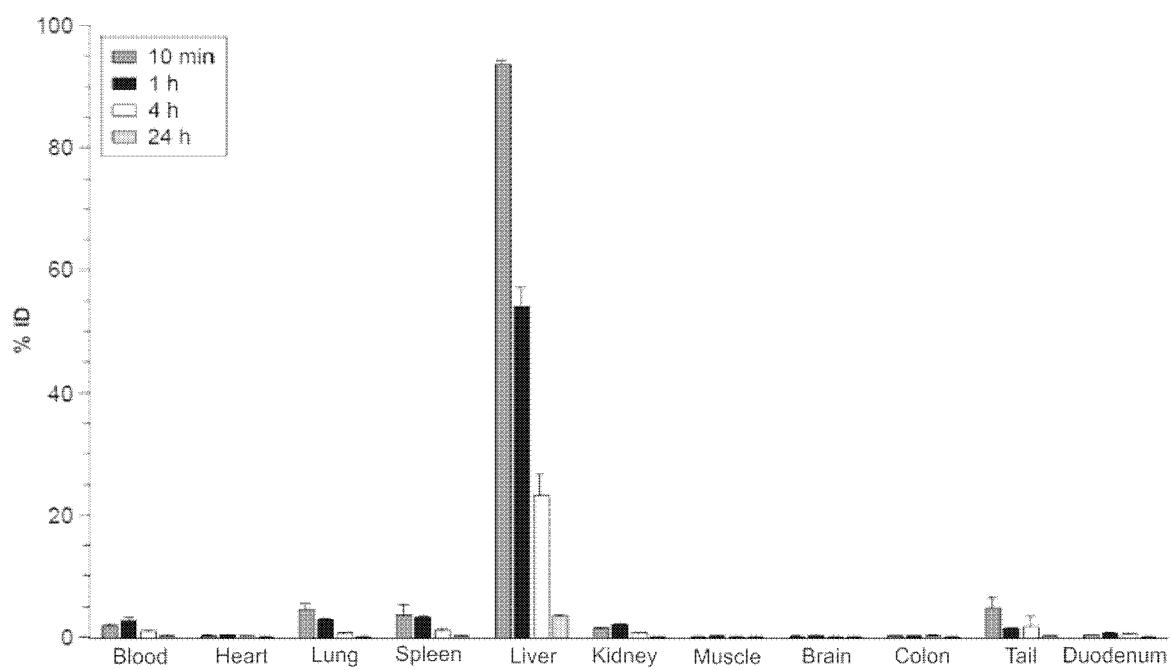
FIG. 5: Organ distribution of doxorubicin modified peptides.

Radioactive labeled peptides where then solved in PBS+3% BSA, heated to 37° C. and injected into the tail vein of WAG/RJ rats. Animals where then euthanized at the indicated time points (FIG. 5), Organs were explanted and measured using a gamma counter. Four animals were measured per time point. FIG. 5 shows the organ distribution of the doxorubicin modified peptides by indicating the average radiation measured per organ as percentage of the injected dose. As demonstrated in FIG. 5, liver tropism is not impaired by the N-terminal modification of the HBV preS peptides with doxorubicin.

Figure 6A:
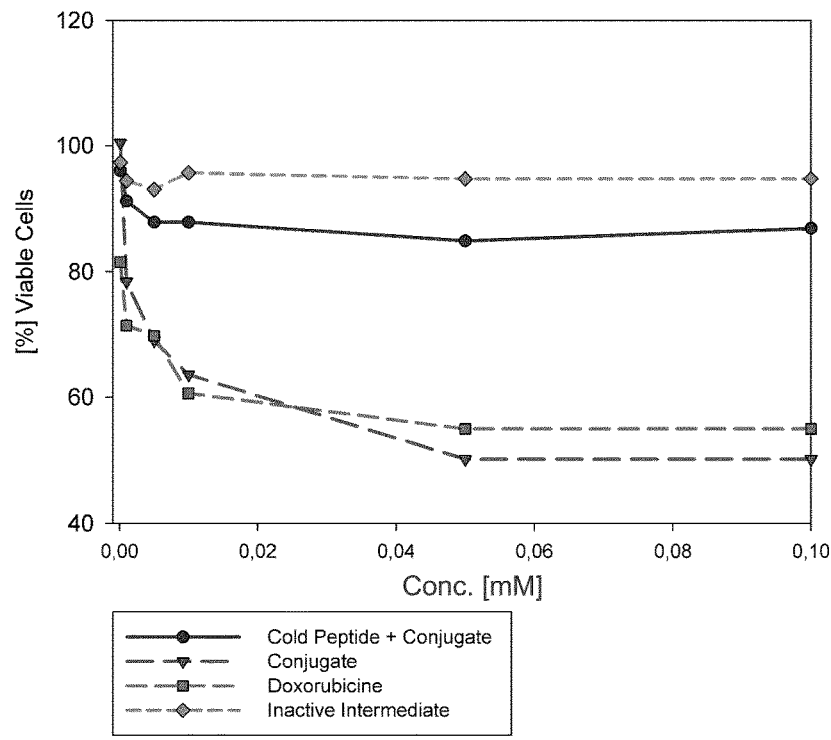
Figure 6B:
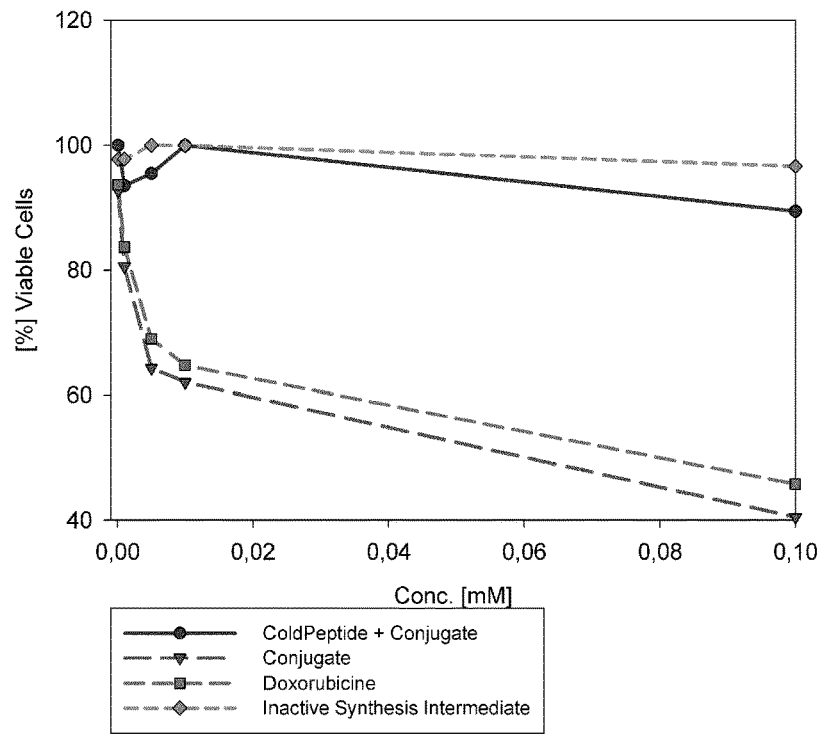

Next it was analyzed if the modified doxorubicin is still cytotoxic to cells. In this experiment primary mouse hepatocytes isolated from C57BL/6 mice as described in Galle et al., (1994) (37) were incubated and reseeded in 96 well flat bottom plates to form a confluent cell layer. 24 h post seeding, cells were incubated with either the synthesized peptides (Conjugate), an inactive synthesis intermediate of doxorubicin, doxorubicin alone and as an additional control the cells were preincubated for 30 minutes using unmodified peptides without addition of doxorubicin (Cold Peptide) followed by the synthesized peptide (conjugate) at the indicated concentrations (FIGS. 6A and 6B). The cells were then incubated for 12 h (FIG. 6A) or 24 h (FIG. 6B), respectively. After incubation an MTT assay (Cell proliferation Kit, Roche Mannheim Germany) was performed as indicated by the manufacturer's instructions to determine remaining cell viability. The results are shown in FIGS. 6A and 6B (Cell Viability Assay).

FIG. 6a (12 h Measurement):

Primary Mouse Hepatocytes were incubated for 12 h with either doxorubicin alone, doxorubicin coupled to the above shown N-terminally modified preS peptides (Conjugate), or an inactive synthesis intermediate of doxorubicin. Preincubation with unmodified preS peptides (Cold Peptide) for 30 minutes followed by incubation with the conjugate served as receptor specific interaction control.

FIG. 6b (24 h Measurement):

Primary Mouse Hepatocytes were incubated for 12 hours with either doxorubicin alone, doxorubicin coupled to the above shown N-terminally modified preS peptides (conjugate), or an inactive synthesis intermediate of doxorubicin. Preincubation with unmodified preS peptides (Cold Peptide) for 30 minutes followed by incubation with the conjugate served as receptor specific interaction control.

Incubation of primary mouse hepatocytes with either doxorubicin alone or Myristoyl-[K-Doxorubicin]-NLSTSNPLGFFPDHQLDPy (SEQ ID NO:21)-amide (HBVpreS/myr-[K-Doxorubicin]3-20y) peptides shows significant cytotoxic effects after 12 h and 24 h incubation. Incubation with an inactive synthesis intermediate of the coupling reaction does not show any toxicity. Furthermore, blocking of the peptide specific receptor by pre-incubating the cells with unmodified preS peptides for 30 minutes prior for treating the cells with Myristoyl-[K-Doxorubicin]-NLST-SNPLGFFPDHQLDPy (SEQ ID NO:21)-amide (HBVpreS/myr-[K-Doxorubicin]3-20y), completely abrogates the cytotoxic effect of the modified peptides.

Figure 7:
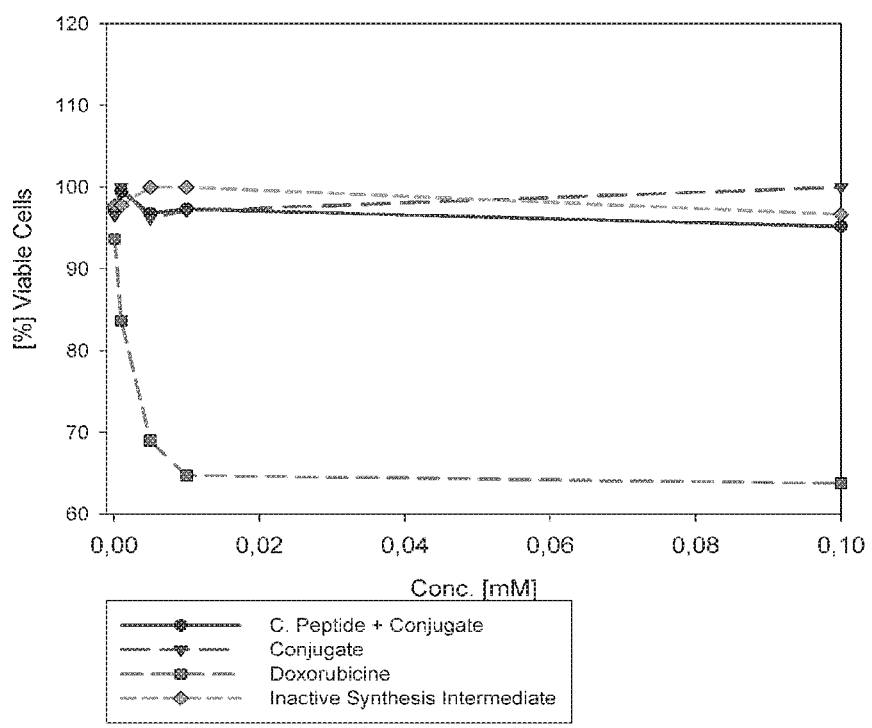
FIG. 7: Cell Viability Assay with HepG2 cells. 12 h measurement of HepG2 cells incubated for 12 h with doxorubicin coupled to N-terminally modified preS peptides (Conjugate) and controls.

As an additional control HepG2 were incubated cells for 12 h under the same conditions as indicated above. HepG2 cells do not express the specific peptide receptor. For this reason HepG2 cells should not be affected by the observed cytotoxic effect of the Myristoyl-[K-Doxorubicin]-NLST-SNPLGFFPDHQLDPy (SEQ ID NO:21)-amide (HBVpreS/myr-[K-Doxorubicin]3-20y) peptides if the observed effect is peptide and receptor specific. The results of this experiment are shown in FIG. 7. FIG. 7 (12 h Measurement): HepG2 cells were incubated for 12 hours with either doxorubicin alone, doxorubicin coupled to the above shown N-terminally modified preS peptides (Conjugate), or an inactive synthesis intermediate of doxorubicin. Preincubation with unmodified preS peptides (Cold Peptide; C. Peptide) for 30 min followed by incubation with the conjugate served as receptor specific interaction control.

As shown in FIG. 7, Myristoyl-[K-Doxorubicin]-NLST-SNPLGFFPDHQLDPy (SEQ ID NO:21)-amide (HBVpreS/myr-[K-Doxorubicin]3-20y) peptides show no cytotoxic activity on cells not expressing the peptide specific receptor, while doxorubicin alone is still showing significant cytotoxicity after 12 h of incubation.

Example 4

Liver Specificity of N-Terminally Modified HBVpreS Peptides Coupled to Levofloxacin for the Treatment of Liver Stage Malaria Levofloxacin coupled peptides have been synthesized as described herein. Briefly, FMOC protected solid phase peptide synthesis was used to synthesize the peptide backbone (KNLSTSNPLGFFPDHQLDP), Levofloxacin was then coupled to the peptide backbone using amid formation. The resulting peptide was the purified by HPLC and purity was analyzed by Mass Spectrometry. Purity of the resulting peptide was 95% or higher.

A sketch of the modified peptide is shown below:

Myristoyl[K-Levofloxacin]-NLSTSNPLGFFPDHQLDPy (SEQ ID NO:21)-amide (HBVpreS/myr-[K-Levofloxacin]3-20y)

In order to show that the resulting synthesized peptide was still liver specific, the above sketched peptide was labeled C-terminally with radioactive $^{131}$Iodine using the chloramine T method as described in (36) and as described above. Radioactive labeled peptides where then solved in PBS+3% BSA, heated to 37° C. and injected into the tail vein of WAG/RJ rats. The animals were then narcotized using Isoflurane and peptide distribution was monitored using a small animal PET scanner. Images were taken at the indicated time points to monitor peptide distribution in the animals.

Figure 8A:
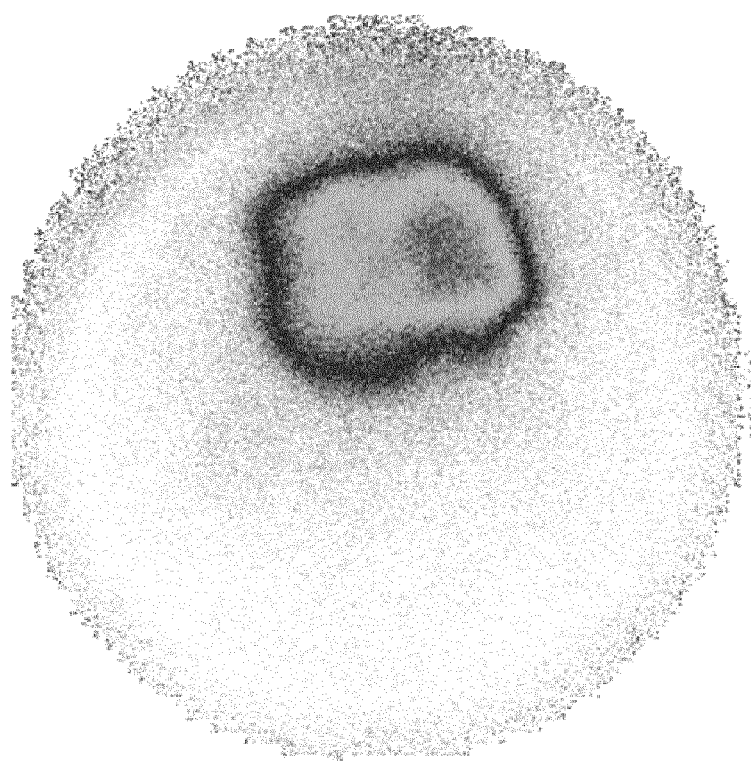
FIG. 8A PET summary image of a rat injected with HBVpreS/myr-[K-Levofloxacin]3-20y-$^{131}$I covering 0-20 minutes post injection.

The images 8A to 8D are summary images covering the indicated time points:

FIG. 8A: PET summary image of a rat injected with Myristoyl-[K-Levofloxacin]-NLSTSNPLGFFPDHQLDPy (SEQ ID NO:21)-$^{131}$I (HBVpreS/myr-[K-Levofloxacin]3-20y-$^{131}$I) covering 0-20 minutes post injection. Almost 100% of all radiation is found in the liver.

Figure 8B:
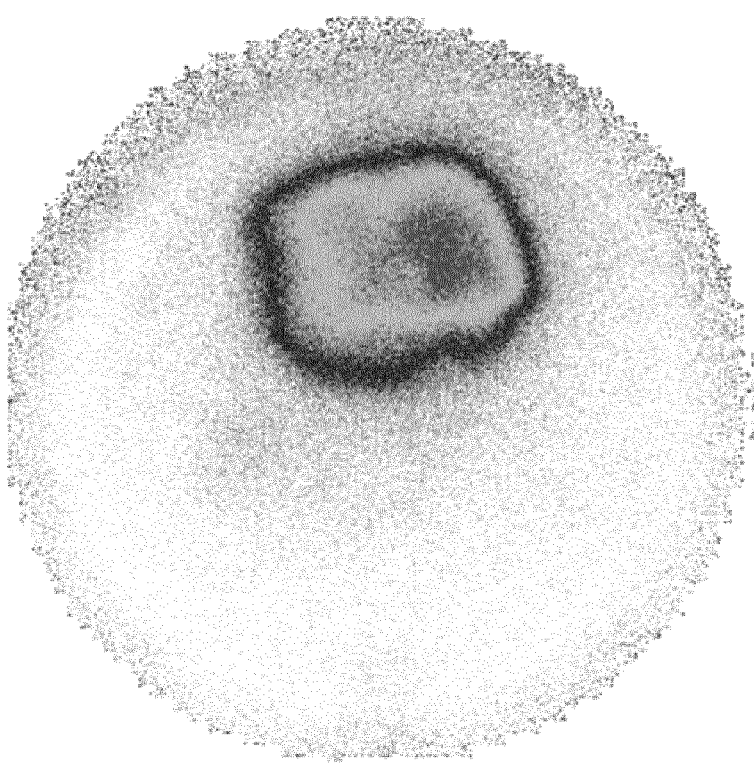
FIG. 8B PET summary image of a rat injected with Myristoyl-[K-Levofloxacin]-NLSTSNPLGFFPDHQLDPy (SEQ ID NO:21)-$^{131}$I (HBVpreS/myr-[K-Levofloxacin]3-20y-$^{131}$I) covering 20-40 minutes post injection.

FIG. 8B: PET summary image of a rat injected with Myristoyl-[K-Levofloxacin]-NLSTSNPLGFFPDHQLDPy (SEQ ID NO:21)-$^{131}$I (HBVpreS/myr-[K-Levofloxacin]3-20y-$^{131}$I) covering 20-40 minutes post injection. Almost 100% of all radiation is found in the liver.

Figure 8C:
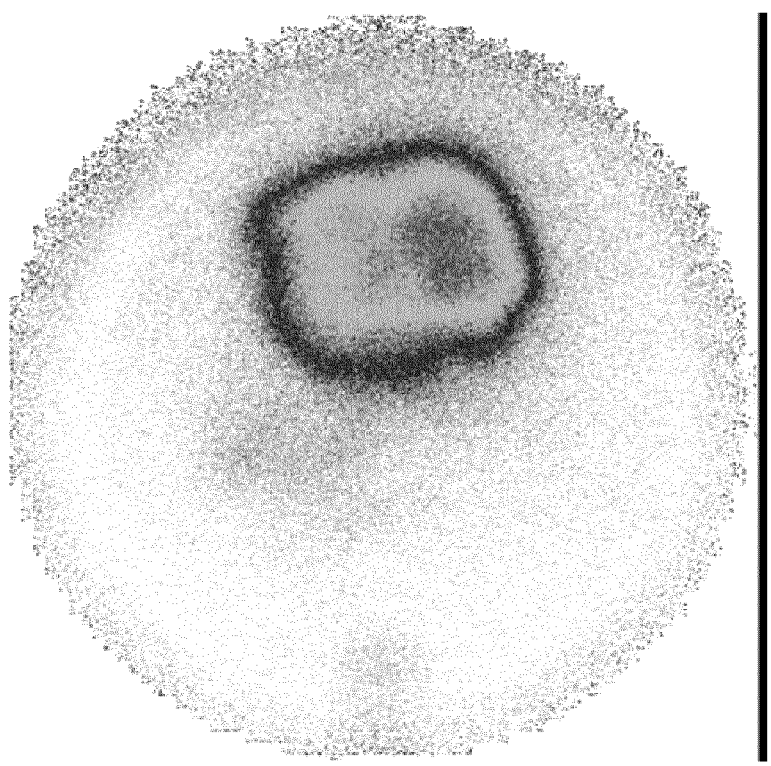
FIG. 8C PET summary image of a rat injected with Myristoyl-[K-Levofloxacin]-NLSTSNPLGFFPDHQLDPy-$^{131}$I (HBVpreS/myr-[K-Levofloxacin]3-20y-$^{131}$I) covering 40-60 minutes post injection.
Figure 8D:
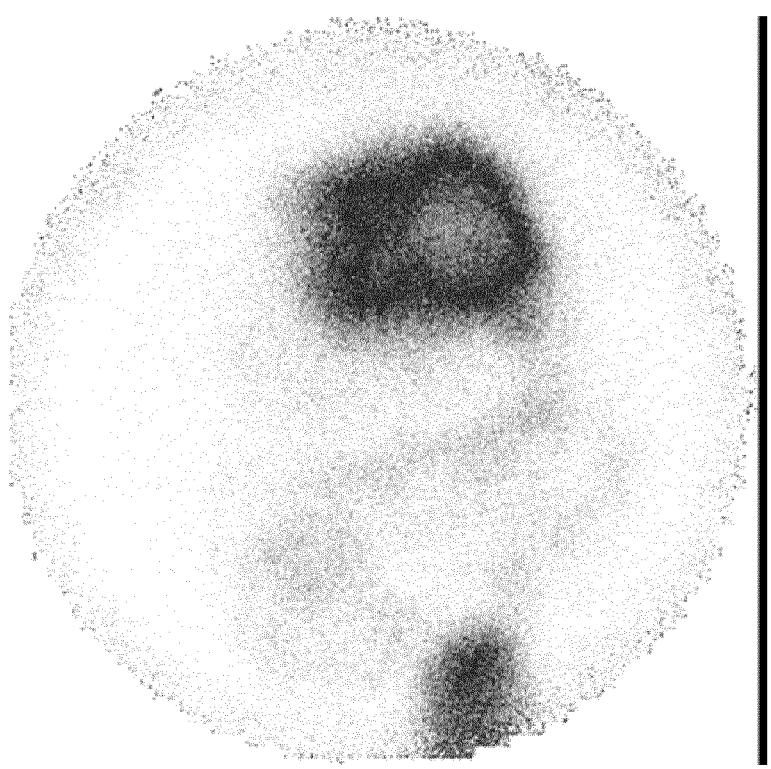
FIG. 8D PET summary image of a rat injected with Myristoyl-[K-Levofloxacin]-NLSTSNPLGFFPDHQLDPy (SEQ ID NO:21)-$^{131}$I (HBVpreS/myr-[K-Levofloxacin]3-20y-$^{131}$I) measured for 10 min 6 h post injection.

FIG. 8C: PET summary image of a rat injected with Myristoyl-[K-Levofloxacin]-NLSTSNPLGFFPDHQLDPy (SEQ ID NO:21)-$^{131}$I (HBVpreS/myr-[K-Levofloxacin] 3-20y-$^{131}$I) covering 40-60 minutes post injection. Most of the radiation is found in the liver, mild enrichment observed in the intestine and bladder FIG. 8D: PET summary image of a rat injected with Myristoyl-[K-Levofloxacin]-NLSTSNPLGFFPDHQLDPy (SEQ ID NO:21)-$^{131}$I (HBVpreS/myr-[K-Levofloxacin]3-20y-$^{131}$I) measured for 10 minutes 6 h post injection. Most of the radiation is still found in the liver, however clear accumulation in of radiation in the intestines and the bladder can be observed.

These experiments demonstrate that Myristoyl-[K-Levofloxacin]-NLSTSNPLGFFPDHQLDPy (SEQ ID NO:21)-$^{131}$I (HBVpreS/myr-[K-Levofloxacin]3-20y-131I) peptides enrich specifically in the liver of WAG/RJ rats, where they are taken up by hepatocytes and traces of radioactivity can be found in the gut and the bladder of the animals 6 h post injection.

The features disclosed in the foregoing description, in the claims and/or in the accompanying drawings may, both separately and in any combination thereof, be material for realizing the invention in diverse forms thereof.

REFERENCES

1. Seeger, C. & Mason, W. S. Hepatitis B virus biology. Microbiol Mol Biol Rev 64, 51-68 (2000).
2. Nassal, M. Hepatitis B virus morphogenesis. Curr Top Microbiol Immunol 214, 297-337 (1996).
3. Gripon, P., Le Seyec, J., Rumin, S. & Guguen-Guillouzo, C. Myristylation of the hepatitis B virus large surface protein is essential for viral infectivity. Virology 213, 292-299 (1995).
4. Le Seyec, J., Chouteau, P., Cannie, I., Guguen-Guillouzo, C. & Gripon, P. Infection process of the hepatitis B virus depends on the presence of a defined sequence in the pre-S1 domain. J Virol 73, 2052-2057 (1999).
5. Juliano R L (1988) Factors affecting the clearance kinetics and tissue distribution of liposomes, microspheres, and emulsions. Adv Drug Deliv Rev 2: 31-54.
6. Hashida M and Takakura Y (1994) Pharmacokinetics in design of polymeric drug delivery systems. J Control Release 31: 163-171.
7. Lu, X. M., Fischman, A. J., Jyawook, S. L., Hendricks, K., Tompkins, R. G. and Yarmush, M. L. (1994) Antisense DNA delivery in vivo: liver targeting by receptor-mediated uptake. J. Nucl. Med. 35, 269-275.
8. Kasuya T, Kuroda S. Nanoparticles for human liver-specific drug and gene delivery systems: in vitro and in vivo advances. Expert Opin Drug Deliv. 2009 January; 6(1):39-52. Review. PubMed PMID: 19236207.
9. Yamada T, Iwasaki Y, Tada H, Iwabuki H, Chuah M K, VandenDriessche T, Fukuda H, Kondo A, Ueda M, Seno M, Tanizawa K, Kuroda S. Nanoparticles for the delivery of genes and drugs to human hepatocytes. Nat Biotechnol. 2003 August; 21(8):885-90. Epub 2003 Jun. 29. PubMed PMID: 12833071
10. Gripon, P., Cannie, I. & Urban, S. Efficient inhibition of hepatitis B virus infection by acylated peptides derived from the large viral surface protein. J Virol 79, 1613-1622 (2005).
11. Chen, K. F., H. C. Yu, et al. (2010). "Synergistic interactions between sorafenib and bortezomib in hepatocellular carcinoma involve PP2A-dependent Akt inactivation." *J Hepatol* 52(1): 88-95.
12. Czauderna, P., G. Mackinlay, et al. (2002). "Hepatocellular carcinoma in children: results of the first prospective study of the International Society of Pediatric Oncology group." *J Clin Oncol* 20(12): 2798-2804.
13. Javle, M. and C. T. Hsueh (2009). "Updates in Gastrointestinal Oncology—insights from the 2008 44th annual meeting of the American Society of Clinical Oncology." *J Hematol Oncol* 2: 9.
14. Lee, J., J. O. Park, et al. (2004). "Phase II study of doxorubicin and cisplatin in patients with metastatic hepatocellular carcinoma." *Cancer Chemother Pharmacol* 54(5): 385-390.
15. Mendelsohn, J. and J. Baselga (2000). "The EGF receptor family as targets for cancer therapy." *Oncogene* 19(56): 6550-6565.
16. Patt, Y. Z., M. M. Hassan, et al. (2003). "Phase II trial of systemic continuous fluorouracil and subcutaneous recombinant interferon Alfa-2b for treatment of hepatocellular carcinoma." *J Clin Oncol* 21(3): 421-427.
17. Richly, H., B. Schultheis, et al. (2009). "Combination of sorafenib and doxorubicin in patients with advanced hepatocellular carcinoma: results from a phase I extension trial." *Eur J Cancer* 45(4): 579-587.
18. Falcone, A., S. Ricci, et al. (2007). "Phase III trial of infusional fluorouracil, leucovorin, oxaliplatin, and irinotecan (FOLFOXIRI) compared with infusional fluorouracil, leucovorin, and irinotecan (FOLFIRI) as first-line treatment for metastatic colorectal cancer: the Gruppo Oncologico Nord Ovest." *J Clin Oncol* 25(13): 1670-1676.
19. Javle, M. and C. T. Hsueh (2009). "Updates in Gastrointestinal Oncology—insights from the 2008 44th annual meeting of the American Society of Clinical Oncology." *J Hematol Oncol* 2: 9.
20. Sagar, J., K. Sales, et al. (2010). "Lowering the apoptotic threshold in colorectal cancer cells by targeting mitochondria." *Cancer Cell Int* 10: 31.
21. Seymour, M. T., T. S. Maughan, et al. (2007). "Different strategies of sequential and combination chemotherapy for patients with poor prognosis advanced colorectal cancer (MRC FOCUS): a randomised controlled trial." *Lancet* 370(9582): 143-152.
22. Tournigand, C., T. Andre, et al. (2004). "FOLFIRI followed by FOLFOX6 or the reverse sequence in advanced colorectal cancer: a randomized GERCOR study." *J Clin Oncol* 22(2): 229-237.
23. Kappe, S. H., A. M. Vaughan, et al. (2010). "That was then but this is now: malaria research in the time of an eradication agenda." *Science* 328(5980): 862-866.
24. Goodman, C. D., V. Su, et al. (2007). "The effects of anti-bacterials on the malaria parasite *Plasmodium falciparum*." *Mol Biochem Parasitol* 152(2): 181-191.24.

25. Zeuzem, S. (2004). "Heterogeneous virologic response rates to interferon-based therapy in patients with chronic hepatitis C: who responds less well?" *Ann Intern Med* 140(5): 370-381.
26. McHutchison, J. G., G. T. Everson, et al. (2009). "Telaprevir with peginterferon and ribavirin for chronic HCV genotype 1 infection." *N Engl J Med* 360(18): 1827-1838.
27. Nelson, D R, Ghalib, R H, Sulkowski, M, et al. Efficacy and safety of the cyclophilin inhibitor Debio 025 in combination with pegylated interferon alpha-2a and ribavirin in previously null-responder genotype 1 HCV patients. Presented at the 44th Annual Meeting of the European Association for the Study of the Liver, Copenhagen, Denmark; Apr. 22-26, 2009; abstract #95
28. (2009). "EASL Clinical Practice Guidelines: management of chronic hepatitis B." *J Hepatol* 50(2): 227-242.
29. Liaw, Y. F., N. Leung, et al. (2005). "Asian-Pacific consensus statement on the management of chronic hepatitis B: a 2005 update." *Liver Int* 25(3): 472-489.
30. Lok, A. S. and B. J. McMahon (2009). "Chronic hepatitis B: update 2009." *Hepatology* 50(3): 661-662.
31. Meng, S., B. Wei, et al. (2009). "TAT peptides mediated small interfering RNA delivery to Huh-7 cells and efficiently inhibited hepatitis C virus RNA replication." *Intervirology* 52(3): 135-140.
32. de Koning, M. C., G. A. van der Marel, et al. (2003). "Synthetic developments towards PNA-peptide conjugates." *Curr Opin Chem Biol* 7(6): 734-740.
33. Zatsepin, T. S., J. J. Turner, et al. (2005). "Conjugates of oligonucleotides and analogues with cell penetrating peptides as gene silencing agents." *Curr Pharm Des* 11(28): 3639-3654.
34. Kornhuber, J., P. Tripal, et al. (2008). "Identification of new functional inhibitors of acid sphingomyelinase using a structure-property-activity relation model." *J Med Chem* 51(2): 219-237.
35. Gastaminza, P., C. Whitten-Bauer, et al. (2010). "Unbiased probing of the entire hepatitis C virus life cycle identifies clinical compounds that target multiple aspects of the infection." *Proc Natl Acad Sci USA* 107(1): 291-296.
36. Eisenhut, M. and W. Mier (2011). Radioiodination Chemistry and Radioiodinated Compounds Handbook of Nuclear Chemistry. A. Vértes, S. Nagy, Z. Klencsár, R. G. Lovas and F. Rosch, Springer US: 2121-2141.
37. Galle, P. R., Hagelstein, J., Kommerell, B., Volkmann, M., Schranz, P., and Zentgraf, H., Gastroenterology 106: 664-673 (1994).
38. Friedman R, Caflisch A. Discovery of plasmepsin inhibitors by fragment-based docking and consensus scoring. ChemMedChem. 2009 August; 4(8):1317-26. PubMed PMID: 19472268.
39. Gamo F J, Sanz L M, Vidal J, de Cozar C, Alvarez E, Lavandera J L, Vanderwall D E, Green D V, Kumar V, Hasan S, Brown J R, Peishoff C E, Cardon L R, Garcia-Bustos J F. Thousands of chemical starting points for antimalarial lead identification. Nature. 2010 May 20; 465(7296):305-10. PubMed PMID: 20485427
40. Friesen J, Silvie O, Putrianti E D, Hafalla J C, Matuschewski K, Borrmann S. Natural immunization against malaria: causal prophylaxis with antibiotics. Sci-Transl Med. 2010 Jul. 14; 2(40):40ra49. PubMed PMID: 20630856.

The invention claimed is:

1. A hydrophobic modified peptide of the formula

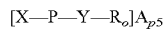

[X—P—Y—R$_o$]A$_{p5}$ wherein P is a peptide having the amino acid sequence NPLGFXaaP (SEQ ID NO: 1), wherein Xaa is F;

X is an amino acid sequence having a length of m amino acids, wherein one or more of the amino acids of X carry one or more groups for hydrophobic modification selected from acylation comprising myristoyl (C 14) or stearoyl (C 18);

m is at least 4;

Y is an amino sequence having a length of n amino acids, wherein n is 0 or at least 1;

m+n≥11

R is a C-terminal modification of said hydrophobic modified peptide with an amide and o is 0 or at least 1, A is an anchor group selected from ester, ether, disulfide, amide, thiol, thioester, p is 0 or at least 1, wherein one or more drug(s) is/are coupled or linked to one or more amino acid(s) of X.

2. The hydrophobic modified peptide according to claim 1, wherein m is 4 to 19 and/or n is 0 to 78.

3. The hydrophobic modified peptide according to claim 1, wherein the one or more drug(s) is/are linked to said peptide via a linker or spacer.

4. The hydrophobic modified peptide according to claim 3, wherein the linker or spacer is cleaved by a hepatocellular proteolytic enzyme.

5. The hydrophobic modified peptide according to claim 4, wherein the enzyme is selected from the group consisting of cytochrome P450, a proteases of the endocytic pathway, a lyase of the endocytic pathway, matrix-metallo-protease 1 (MMP1), matrix-metallo-protease 2 (MMP2), matrix-metallo-protease 7 (MMP7), matrix-metallo-protease 9 (MMP9), matrix-metallo-protease 12 (MMP12), and matrix-metallo-protease 7 (MMP7).

6. The hydrophobic modified peptide according to claim 4, wherein the linker or spacer comprises the peptide sequences GCHAK (SEQ ID NO: 19) or RPLALWRS (SEQ ID NO:20).

7. The hydrophobic modified peptide according to claim 1, wherein one or more drug(s) is/are coupled to one or more amino acid(s) of X having an amino group in a side chain.

8. The hydrophobic modified peptide according to claim 7, wherein the amino acid(s) having an amino group in a side chain is/are lysine.

9. The hydrophobic modified peptide according to claim 1, wherein the one or more amino acid(s) having an amino group in a side chain are located at the N-terminus of X.

10. The hydrophobic modified peptide according to claim 9, wherein 1 to 11 amino acids having an amino group in a side chain are located at the N-terminus of X.

11. The hydrophobic modified peptide according to claim 10, wherein the drug(s) is/are coupled to one or more of the 1 to 11 amino acid(s) having an amino group in a side chain via an activated ester.

12. The hydrophobic modified peptide according to claim 1, wherein the drug(s) is/are coupled to the amino acid(s) of X by using one or more methods selected from formation of amides by the reaction of an amine and activated carboxylic acids, disulfide linkage using two thiols or one thiol that specifically reacts with pyridyl disulfides;

thioether formation using maleimides or haloacetyls and a thiol component;

amidine formation using an imidoester and an amine;

hydrazide linkage using carbonyls and hydrazides;

amine linkage using carbonyls and amines under reductive conditions;

triazol formation using nitriles and azides;

thiourea formation using isothiocyanates and amines;

formation of esters by the reaction of an alcohol and activated carboxylic acids; and formation of ethers by the reaction of an alcohol and alkyl halides.

13. The hydrophobic modified peptide according to claim 1, wherein the hydrophobic modification is by acylation with myristoyl (C 14).

14. The hydrophobic modified peptide according to claim 1, wherein the hydrophobic modification is by acylation with stearoyl (C 18).

15. The hydrophobic modified peptide according to claim 1, wherein said peptide comprises of SEQ ID NOs: 2 to 13 with an amino acid sequence of different viral species, strains or subtypes selected from the genotypes consisting of HBC, wooly monkey HBV, or variants thereof.

16. The hydrophobic modified peptide according to claim 1, wherein the drug(s) coupled or linked to one or more amino acid(s) of X is a combination of two or more drugs.

17. The hydrophobic modified peptide according to claim 16, wherein the drug is selected from doxorubicin, a gyrase inhibitors of the fluoroquinilone class, primaquine, clindamycin, azithromycin, ciprofloxacin, doxocycline, atovaquone, rifampicin, and dapsone.

18. The hydrophobic modified peptide according to claim 16, wherein the drug is selected from doxorubicin, oxaliplatin, irinotecan, fluorouracil, -bortezomib, sorafenib, botezomib, erlotinib, interferon-α, cisplatin, and lencovorin.

19. The hydrophobic modified peptide according to claim 17, wherein the drug is selected from the group consisting of primaquine, doxorubicin and a gyrase inhibitors.

20. The hydrophobic modified peptide according to claim 18, wherein the combination of two or more drugs is selected from a combination of bortezumib and doxorubicin; sorafenib and doxorubicin; botezomib and sorafenib; erlotinib and fluorouracil; erlotinib, fluorouracil and interferon-α; cisplatin and doxorubicin; cisplatin, doxorubicin and erlotinib; irinotecan and fluorouracil; irinotecan and erotinib; oxaliplatin and fluorouracil; and FOLFOX (oxaliplatin, fluorouracil, lencovorin).

21. The hydrophobic modified peptide according to claim 1, which is selected from the group consisting of
stearoyl-[K(primaquine)]$_3$-NLSTSNPLGFFPDHQLDP (SEQ ID NO:15),
stearoyl-[K(GCHAK(SEQ ID NO: 19) primaquine)]-NLSTSNPLGFFPDHQLDP (SEQ ID NO:21), myristoyl-[K(Doxocyclin)]$_3$-NLSTSNPLGFFPDHQLDP (SEQ ID NO: 15),
myristoyl-[K(GCHAK(SEQ ID NO: 19) Doxocylin)]$_3$-NLSTSNPLGFFPDHQLDP (SEQ ID NO:15),
myristoyl-[K(Penicillin)]3-NLSTSNPLGFFPDHQLDP (SEQ ID NO:15),
myristoyl-[K(GCHAK(SEQ ID NO: 19)-Penicillin)]$_3$-NLSTSNPLGFFPDHQLDP (SEQ ID NO:15),
myristoyl-[K(Cyclosporine)]$_3$-NLSTSNPLGFFPDHQLDP (SEQ ID NO:15),
myristoyl-[K(GCHAK(SEQ ID NO: 19)-Cyclosporine)]$_3$-NLSTSNPLGFFPDHQLDP (SEQ ID NO:15),
myristoyl-[K(sirolimus)]$_3$-NLSTSNPLGFFPDHQLDP (SEQ ID NO:15),
myristoyl-[K(GCHAK sirolimus)]$_3$-NLSTSNPLGFFPDHQLDP (SEQ ID NO:15),
stearoyl-[K(RPLALWRS(SEQ ID NO: 20) bortezomib)]$_3$-NLSTSNPLGFFPDHQLDP (SEQ ID NO:15),
stearoyl-[K(sorafenib)]$_3$-NLSTSNPLGFFPDHQLDP (SEQ ID NO:15),
stearoyl-[K(RPLALWRS(SEQ ID NO: 20) sorafenib)]$_3$-NLSTSNPLGFFPDHQLDP (SEQ ID NO:15),
stearoyl-[K(Thiazolidinedione)]$_3$-NLSTSNPLGFFPDHQLDP (SEQ ID NO:15),
myristoyl-[K-Levofloxacin]-NLSTSNPLGFFPDHQLDP (SEQ ID NO:21), and
myristoyl-[K-Doxorubicin]-NLSTSNPLGFFPDHQLDP (SEQ ID NO:21).

22. A pharmaceutical composition comprising: at least one hydrophobic modified peptide according to claim 1 and a pharmaceutically acceptable carrier and/or excipient.

23. The hydrophobic modified peptide according to claim 1 or a pharmaceutical composition comprising said peptide for use in the specific delivery of a drug to the liver.

24. The hydrophobic modified peptide or pharmaceutical composition according to claim 23 for use in the treatment of a liver disease or disorder selected from the group consisting of virus-induced hepatitis or cirrhosis, malaria, and a liver tumor.

25. The hydrophobic modified peptide or pharmaceutical composition according to claim 23, wherein the hydrophobic modified peptide is administered to a patient in a dosage ranging from 10 pmol per kg body weight to 20 μmol per kg body weight.

26. The hydrophobic modified peptide or pharmaceutical composition according to claim 25, wherein the hydrophobic modified peptide is administered to a patient in a dosage ranging from 100 nmol per kg body weight to 2 μmol per kg body weight.

27. The hydrophobic modified peptide or pharmaceutical composition according to claim 23, wherein the route of administration is selected from subcutaneous, intravenous, oral, nasal, intramuscular, transdermal, by inhalation, or by suppository.

28. The hydrophobic modified peptide according to claim 7, wherein the one or amino acid(s) of X having the amino group in the side chain is/are selected from lysine, α-amino glycine, α,γ-diaminobutyric acid, ornithine, and α,β-diaminopropionic acid.

29. The hydrophobic modified peptide or pharmaceutical composition according to claim 23, wherein the liver tumor is hepatocellular carcinoma (HCC).

30. The hydrophobic modified peptide or pharmaceutical composition according to claim 23, wherein the hepatitis is caused by hepatitis A, B, C, D, E, F, G and H virus or concomitant hepatitis caused by viruses.

31. The hydrophobic modified peptide according to claim 16, wherein the drug is selected from interferon-α, ribavirin, telepravir, boceprevir, cyclosporine A, tenofovir, and entecavir.

32. The hydrophobic modified peptide according to claim 12, wherein the activated carboxylic acids are NHS-esters or carbodiimides.

33. The hydrophobic modified peptide according to claim 12, wherein the activated carboxylic acids are acid chlorides or carbodiimides.

34. The hydrophobic modified peptide according to claim 10, wherein 1 to 3 amino acids having an amino group in a side chain are located at the N-terminus of X.

35. The hydrophobic modified peptide according to claim 12, wherein the carbonyls are aldehydes.

36. The hydrophobic modified peptide according to claim 17, wherein the combination of two or more drugs is selected from a combinations of primaquine and clindamycin; primaquine and azithromycin; ciprofloxacin, doxocycline and atovaquone; primaquine, ciprofloxacin and rifampicin; and primaquine, rifampicin and dapsone.

37. The hydrophobic modified peptide according to claim 31, wherein the combination of two or more drugs is selected from a combinations of interferon-α and ribavirin; telepravir and ribavirin; telepravir, ribavirin and interferon-α; boceprevir and ribavirin; boceprevir, ribavirin and interferon-α; cyclosporin A and interferon-α; tenofovir and entecavir; tenofovir and interferon-α; entecavir and interferon-α; and tenofovir, entecavir and interferon-α.

38. The hydrophobic modified peptide according to claim 1, wherein the hydrophobic modification of the one or more amino acids of X further comprises an addition of hydrophobic moiety selected from the group consisting of cholesterol, phospholipids, glycolipids, glycerol esters, steroids, ceramids, isoprene, adamantane, farnesol, aliphatic groups, and polyaromatic compounds.

* * * * *